(12) United States Patent
Al-Jaroudi et al.

(10) Patent No.: US 10,294,254 B2
(45) Date of Patent: *May 21, 2019

(54) DNA/DITHIOCARBAMATO PHOSPHINE METAL COMPLEX

(71) Applicants: KING FAHD UNIVERSITY OF PETROLEUM AND MINERALS, Dhahran (SA); KING SAUD UNIVERSITY, Riyadh (SA)

(72) Inventors: Said S. Al-Jaroudi, Dhahran (SA); Ali Alhoshani, Riyadh (SA); Muhammad Altaf, Dhahran (SA); Anvarhusein Abdulkadir Isab, Dhahran (SA)

(73) Assignees: King Fahd University of Petroleum and Minerals, Dhahran (SA); King Saud University, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 16/112,188

(22) Filed: Aug. 24, 2018

(65) Prior Publication Data

US 2018/0362556 A1 Dec. 20, 2018

Related U.S. Application Data

(63) Continuation of application No. 15/993,163, filed on May 30, 2018, now Pat. No. 10,144,749, which is a continuation of application No. 15/351,585, filed on Nov. 15, 2016, now Pat. No. 10,077,280.

(60) Provisional application No. 62/326,389, filed on Apr. 22, 2016.

(51) Int. Cl.

| | |
|---|---|
| A61K 31/66 | (2006.01) |
| C07F 9/50 | (2006.01) |
| A61K 45/06 | (2006.01) |
| G01N 33/574 | (2006.01) |
| C12Q 1/68 | (2018.01) |
| C12Q 1/6886 | (2018.01) |
| A61N 1/30 | (2006.01) |
| A61K 9/00 | (2006.01) |

(52) U.S. Cl.
CPC .......... *C07F 9/5045* (2013.01); *A61K 9/0053* (2013.01); *A61K 31/66* (2013.01); *A61K 45/06* (2013.01); *A61N 1/30* (2013.01); *C12Q 1/6886* (2013.01); *G01N 33/57415* (2013.01); *C12Q 2600/156* (2013.01); *G01N 2800/52* (2013.01)

(58) Field of Classification Search
CPC ..... C07F 9/5045; A61K 31/66; C12Q 1/6886; G01N 33/5715
See application file for complete search history.

(56) References Cited

U.S. PATENT DOCUMENTS

2014/0142065 A1  5/2014  Che

OTHER PUBLICATIONS

Muhammad Altaf, et al., "Synthesis, characterization and anticancer activity of gold(I) complexes that contain tri-tert-butylphosphine and dialkyl dithiocarbamate ligands", European Journal of Medicinal Chemistry, vol. 95, 2015, pp. 464-472.

Muhammad Altaf, et al., "The synthesis, spectroscopic characterization and anticancer activity of new mono and binuclear phosphanegold(I) dithiocarbamate complexes", New Journal of Chemistry, vol. 39. No. 1, 2015, pp. 377-385.

Saira Naeem, et al., "Ring-Closing Metathesis and Nanoparticle Formation Based on Diallyldithiocarbamate Complexes of Gold(I): Synthetic, Structural, and Computational Studies", Inorganic Chemistry, vol. 53, No. 5, 2014, pp. 2404-2416.

Frankline K. Keter, et al., "Phosphinogold(I) Dithiocarbamate Complexes: Effect of the Nature of Phosphine Ligand on Anticancer Properties", Inorganic Chemistry, vol. 53, No. 4, 2014, pp. 2058-2067.

Nazzatush Shimar Jamaludin, et al., "Phosphanegold(I) dithiocarbamates, $R_3PAu[Sc(=S)N(^iPr)CH_2CH_2OH]$ for R=Ph, Cy and Et: Role of phosphane-bound R substituents upon in vitro cytotoxicity against MCF-7R breast cancer cells and cell death pathways", European Journal of Medicinal Chemistry, vol. 67, 2013, pp. 127-141.

Katie Oliver, et al., "Multimetallic complexes of group 10 and 11 metals based on polydentate dithiocarbamate ligands", Dalton Transactions, vol. 40, No. 22, 2011, pp. 5852-5864.

Valentina Gandin, et al., "Cancer cell death induced by phosphine gold(I) compounds targeting thioredoxin reductase", Biochemical Pharmacology, vol. 79, No. 2, 2010, pp. 90-101.

S. Y. Ho, et al., "Crystal structure of (diethyldithiocarbamato)(triethylphosphine)gold(I), $Au[P(C_2H_5)_3][S_2CN(C_2H_5)_2]$", Zeitschrift Fuer Kristallographie—New Crystal Structures, vol. 220, No. 3, 2005, pp. 342-344.

Manuel Bardají, et al., "Synthesis and structural characterization of luminescent gold(I) derivatives with an unsymmetric diphosphine", Dalton Transactions, vol. 23, 2003, pp. 4529-4536.

Manuel Bardají, et al., "Synthesis and Structural Characterization of Luminescent Gold(I) Complexes with Dithiocarbamates", Inorganic Chemistry, vol. 39, No. 16, 2000, pp. 3560-3566.

Christopher K. Mirabelli, et al., "Antitumor activity of Bis(diphenylphosphino)alkanes, Their Gold(I) Coordination Complexes, and Related Compounds", Journal of Medicinal Chemistry, vol. 30, No. 12, 1987, pp. 2181-2190.

H. W. Chen, et al., "Dimethylgold(III) Complexes. Synthesis of Several Compounds with $AuC_2S_2$ Coordination. The Crystal and Molecular Structure of [ $(CH_3)_2AuSC_2H_5]_2$", Inorganica Chimica Acta. vol. 96, No. 2. 1985, pp. 137-149.

C. Kowala, et al., "Coordination Compounds of Group IB Metals III. Triethyl- and triphenyl-phosphine complexes of cuprous, argentous, and aurous N,N-Dialkyldithiocarbamates", Australian Journal of Chemistry, vol. 19, No. 4, 1966, pp. 555-559.

C. Kowala, et al., Coordination Compounds of Group IB Metals. II. Some Tertiary Phosphine and Phosphite Complexes of Gold(I), Australian Journal of Chemistry, vol. 19, No. 4, 1966, pp. 547-554.

G. E. Coates, et al., "Coordination Compounds of Group IB Metals. I. Triethylphosphine Complexes of Gold(I) Mercaptides", Australian Journal of Chemistry, vol. 19, No. 4, 1966, pp. 539-545.

*Primary Examiner* — Sahar Javanmard
(74) *Attorney, Agent, or Firm* — Oblon, McClelland, Maier & Neustadt, L.L.P.

(57) ABSTRACT

Gold(I) complex with mixed ligands as an anticancer agent. The gold(I) ion is coordinated to a dithiocarbamate ligand and a phosphorus-containing ligand (e.g. phosphines). Also described are a pharmaceutical composition incorporating the gold(I) complex, a methods of synthesizing the gold(I) complex, and a method for treating cancer.

5 Claims, 15 Drawing Sheets

Dotted lines show short contacts between different functional groups in the molecules.

FIG. 8A
FIG. 8B
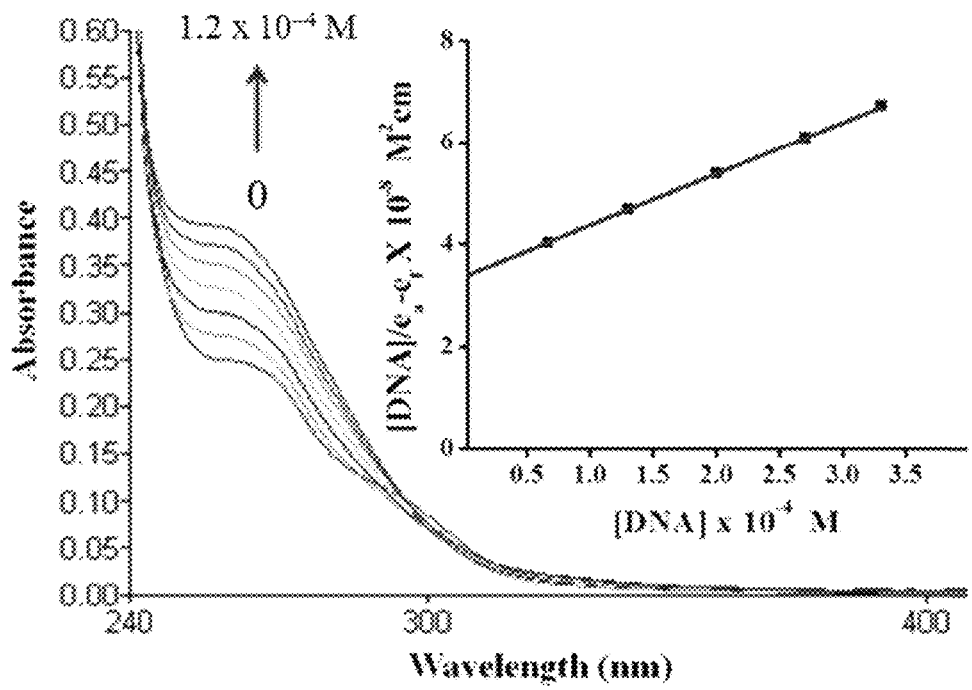
FIG. 8C
FIG. 8D
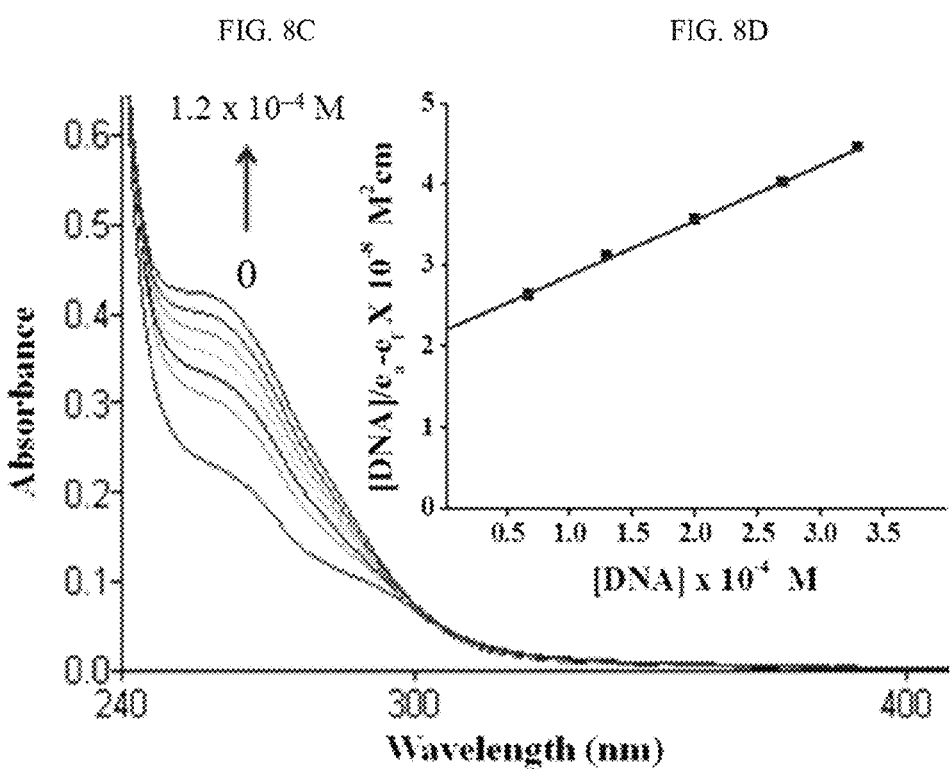

FIG. 8E
FIG. 8F
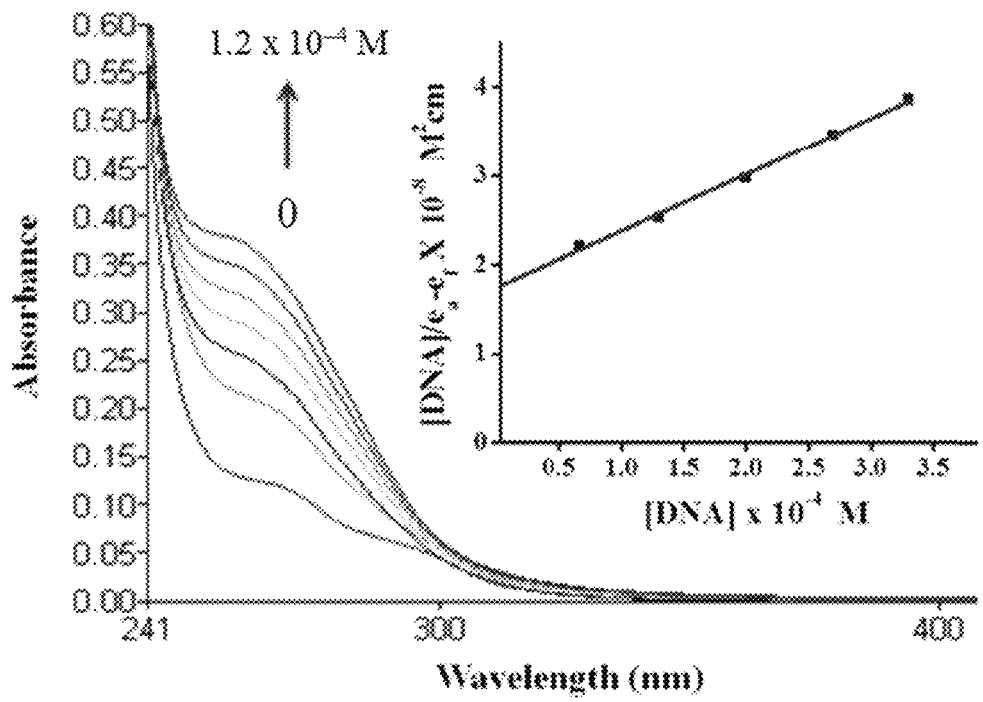
FIG. 8G
FIG. 8H
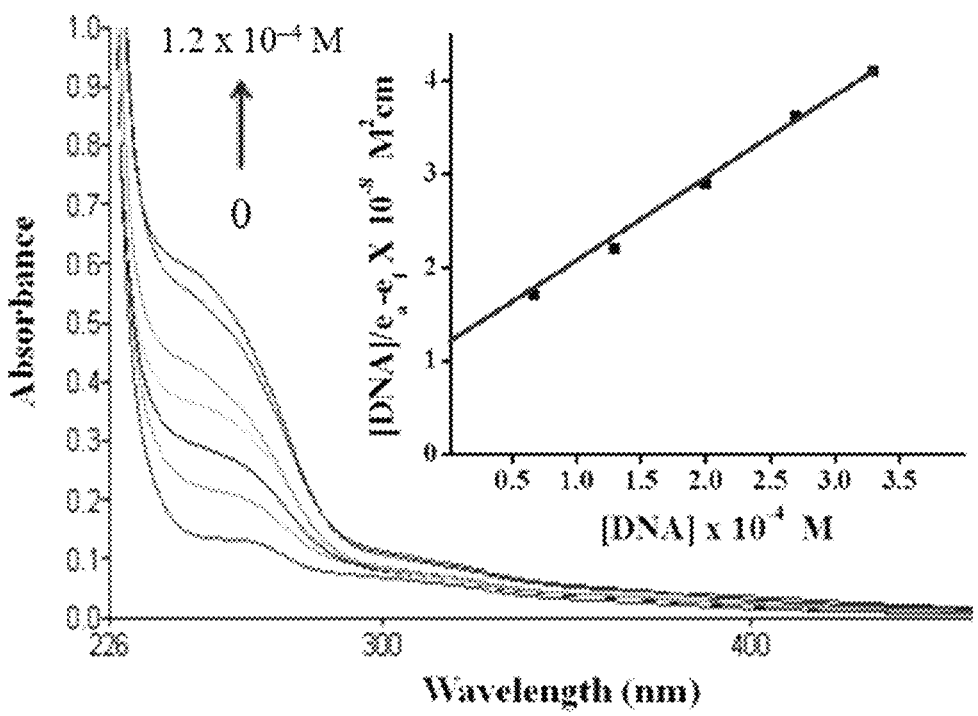

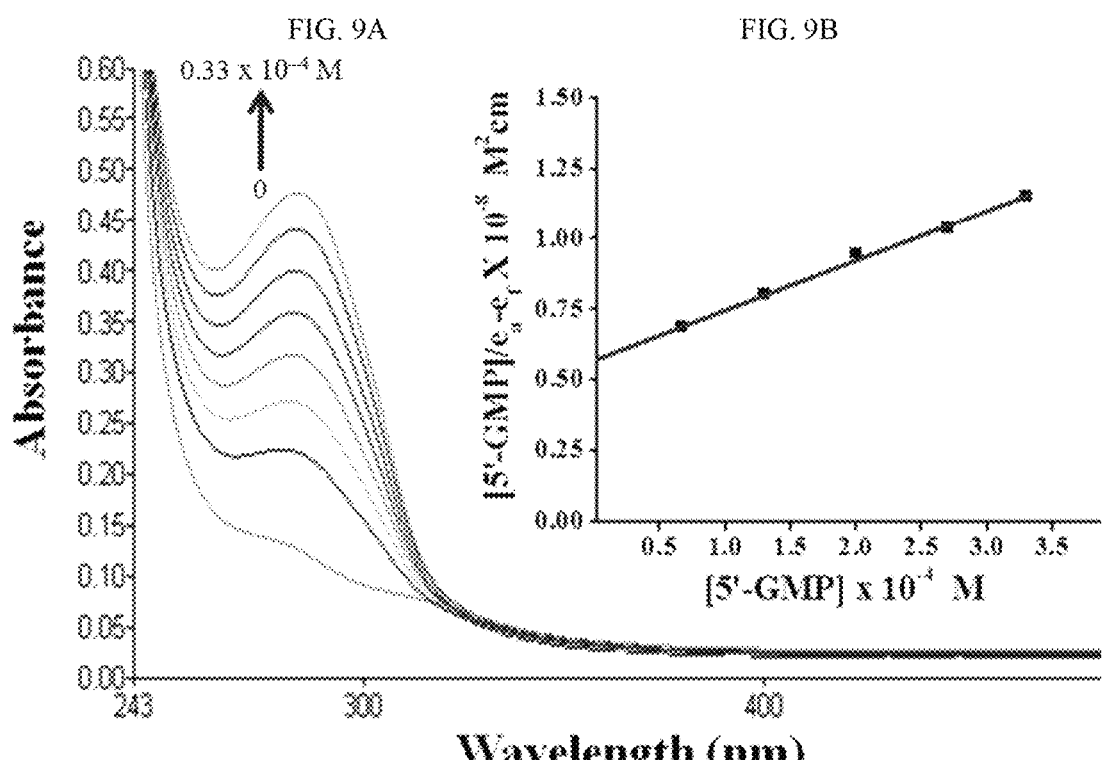
FIG. 9A
FIG. 9B
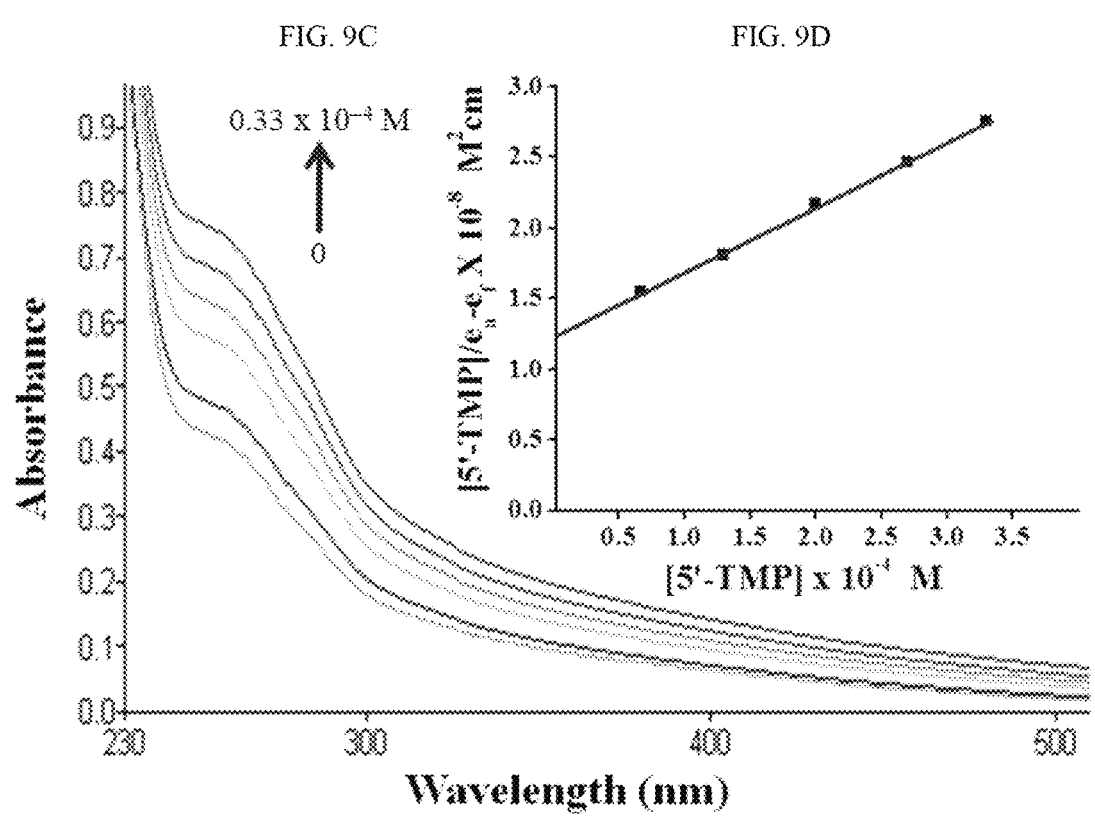
FIG. 9C
FIG. 9D

DNA/DITHIOCARBAMATO PHOSPHINE METAL COMPLEX

RELATED APPLICATIONS

This application is a Continuation of U.S. application Ser. No. 15/993,163, now allowed, having a filing date of May 30, 2018, which is a Continuation of U.S. application Ser. No. 15/351,585, now allowed, having a filing date of Nov. 15, 2016 and claims priority to U.S. Provisional Application No. 62/326,389, having a filing date of Apr. 22, 2016 and which is incorporated herein by reference in its entirety.

STATEMENT OF FUNDING ACKNOWLEDGEMENT

This project was funded by the National Plan for Science and Innovation (MARIFAH)—King Abdulaziz City for Science and Technology (KACST) through the Science and Technology Unit at King Fahd University of Petroleum and Minerals (KFUPM) of Saudi Arabia, award No. 14-MED64-04.

BACKGROUND OF THE DISCLOSURE

Technical Field

The present disclosure relates to therapeutic gold(I) complexes, a pharmaceutical composition thereof, and a method of treating cancer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The field of medicinal inorganic chemistry has gained prominence through the serendipitous discovery of the cytotoxic properties of cisplatin by Rosenberg (Rosenberg, B.; Van Camp, L.; Krigas, T. Inhibition of Cell division in *Escherichia Coli* by electrolysis products from a platinum electrode. *Nature.* 1965, 205, 698-699, incorporated herein by reference in its entirety). Despite the great success of cisplatin and its analogues, the platinum-containing drugs manifests systemic toxicity and clinical inefficiency against resistant tumors, therefore limiting their domain of applicability (Rabik, A. C.; Dolan, E. M. Molecular mechanisms of resistance and toxicity associated with platinating agents. *Cancer Treat. Rev.* 2007, 33, 9, incorporated herein by reference in its entirety). The development of new metallotherapeutic drugs with different pharmacological activity from platinum-containing drugs is one of the major goals of modern bioinorganic and bio-organometallic medicinal chemistry research (Bertrand, B.; Bodio, E; Richard, Picquet, M.; Le Gendre, P.; Casini, A. Gold(I) N-heterocyclic carbene complexes with an "activable" ester moiety: Possible biological applications. *J. Organomet. Chem.* 2105, 775, 124-129; Sadler, J. P.; Sue E. R. The Chemistry of Gold Drugs. *Met.-Based Drugs.* 1994, 1, 107-144; Shaw III, C. F. Gold-Based therapeutic agents. *Chem. Rev.* 1999, 99, 2589-2600; Best, L. S. and Sadler, J. P. Gold Drugs: Mechanism of Action and Toxicity. *Gold Bull.* 1996, 29, 87-93; Van Rijt, H. S.; Sadler, J. P. Current applications and future potential for bioinorganic chemistry in the development of anticancer drugs. *Drug Discovery Today.* 2009, 14, 1089-1097; Pantelic, N; Stanojkovic, T. P.; Zmejkovski, B. B.; Sabo, T. J.; Kaluderovic, G. N. In vitro anticancer activity of gold(III) complexes with some esters of (S,S)-ethylenediamine-N,N'-di-2-propanoic acid. *Eur. J. Med. Chem.* 2015, 90, 766-774; and Al-Jaroudi, S. S.; Fettouhi, M.; Wazeer, M. I. M.; Isab, A. A.; Altuwaijri, S. Synthesis, characterization and cytotoxicity of new gold(III) complexes with 1,2-diaminocyclohexane: Influence of stereochemistry on antitumor activity. *Polyhedron.* 2013, 50, 434-442, each incorporated herein by reference in their entirety). Considerable efforts are being made to circumvent the side effects, to enhance the cytotoxicity profile and to augment the efficacy and specificity of the prevalent antitumor drugs (Fléchon, A.; Rivoire, M.; Droz, J. P. Management of advanced germ-cell tumors of the testis. *Nat. Clin. Pract. Urol.* 2008, 5, 262-276.; and Adams, G.; Zekri, J.; Wong, H.; Walking, J.; Green, J. A. Platinum-based adjuvant chemotherapy for early-stage epithelial ovarian cancer: single or combination chemotherapy. *BJOG.* 2010, 117, 1459-1467, each incorporated herein by reference in their entirety).

Therefore, an objective of this disclosure is to provide a therapeutic gold(I) complex with a large therapeutic index, a composition comprising thereof, and a method for treating cancer.

BRIEF SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

A first aspect of the disclosure relates to a gold(I) complex represented by formula (I):

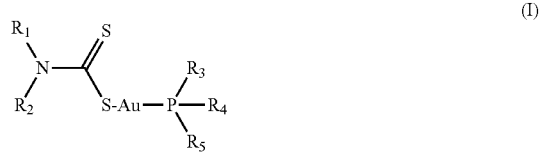

a salt thereof, a solvate thereof, or a combination thereof, where $R_1$ and $R_2$ are independently selected from the group consisting of H, an unsubstituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted arylolefin, an optionally substituted $C_4$-$C_{10}$ alkenyl, and an optionally substituted vinyl;

$R_3$, $R_4$, and $R_5$ are independently selected from the group consisting of H, an optionally substituted $C_1$-$C_3$ alkyl, an optionally substituted $C_3$-$C_5$ cycloalkyl, an optionally substituted cycloalkylalkyl, an optionally substituted arylalkyl, an optionally substituted heteroaryl, an optionally substituted aryl, an optionally substituted heterocyclyl, an optionally substituted arylolefin, an optionally substituted vinyl, an optionally substituted alkylamino, an optionally substituted arylamino, an optionally substituted alkylarylamino, an optionally substituted alkoxy, and an optionally substituted aryloxy; and with the proviso that $R_1$, $R_2$, $R_3$, $R_4$, and $R_5$ are not each an ethyl.

In one embodiment, $R_1$ and $R_2$ are the same unsubstituted alkyl group, and $R_3$, $R_4$, and $R_5$ are the same optionally substituted $C_1$-$C_3$ alkyl group.

In one embodiment, $R_1$ and $R_2$ are methyls, and $R_3$, $R_4$, and $R_5$ are selected from the group consisting of methyl, ethyl, and isopropyl.

In one embodiment, $R_1$ and $R_2$ are ethyls, and $R_3$, $R_4$, and $R_5$ are methyls.

In one embodiment, $R_1$ and $R_2$ are independently an unsubstituted alkyl selected from the group consisting of isopropyl, sec-butyl, isobutyl, and tert-butyl.

A second aspect of the disclosure relates to a composition comprising the gold(I) complex of the first aspect, and a pharmaceutically acceptable carrier or excipient.

In one embodiment, the composition comprises 0.01-50 µM of the gold(I) complex relative to the total composition.

In one embodiment, the composition further comprises a chemotherapeutic agent.

In one embodiment, the chemotherapeutic agent is at least one selected from the group consisting of aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab.

A third aspect of the disclosure relates to a method for treating cancer, comprising administering the composition of the second aspect to a subject in need thereof.

In one embodiment, the method further comprises measuring a concentration of a biomarker and/or detecting a mutation in the biomarker before and/or after the composition is administered.

In one embodiment, the biomarker is at least one selected from the group consisting of BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ.

In one embodiment, the concentration of the biomarker is measured with an ELISA assay.

In one embodiment, the mutation in the biomarker is detected with at least one method selected from the group consisting of a polymerase chain reaction assay, a DNA microarray, multiplex ligation-dependent probe amplification, single strand conformational polymorphism, denaturing gradient gel electrophoresis, heteroduplex analysis, and restriction fragment length polymorphism.

In one embodiment, the cancer is resistant to cisplatin.

In one embodiment, the cancer is breast cancer.

In one embodiment, the subject is a mammal.

In one embodiment, an effective amount of the gold(I) complex, the salt thereof, the solvate thereof, or a combination thereof is in a range of 1-100 mg/kg.

In one embodiment, the composition is administered once daily for at least 2 days.

In one embodiment, the composition is administered orally.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 8A is an overlay of the absorption spectra of complex 1 in the absence and presence of CT DNA.

FIG. 8B is a plot of $[DNA]/(e_a-e_f)$ against [DNA] for the titration of CT DNA with complex 1.

FIG. 8C is an overlay of the absorption spectra of complex 2 in the absence and presence of CT DNA.

FIG. 8D is a plot of $[DNA]/(e_a-e_f)$ against [DNA] for the titration of CT DNA with complex 2.

FIG. 8E is an overlay of the absorption spectra of complex 3 in the absence and presence of CT DNA.

FIG. 8F is a plot of $[DNA]/(e_a-e_f)$ against [DNA] for the titration of CT DNA with complex 3.

FIG. 8G is an overlay of the absorption spectra of complex 4 in the absence and presence of CT DNA.

FIG. 8H is a plot of $[DNA]/(e_a-e_f)$ against [DNA] for the titration of CT DNA with complex 4.

FIG. 9A is an overlay of the absorption spectra of complex 4 in Tris-HCl buffer at various concentrations of 5'-GMP at 25° C.

FIG. 9B is a plot of $[5'-GMP]/(e_a-e_f)$ against [5'-GMP] for the titration of 5'-GMP with complex 4.

FIG. 9C is an overlay of the absorption spectra of complex 4 in Tris-HCl buffer at various concentrations of 5'-TMP at 25° C.

FIG. 9D is a plot of $[5'-TMP]/(e_a-e_f)$ against [5'-TMP] for the titration of 5'-TMP with complex 4.

DETAILED DESCRIPTION OF THE EMBODIMENTS

Figure 1:
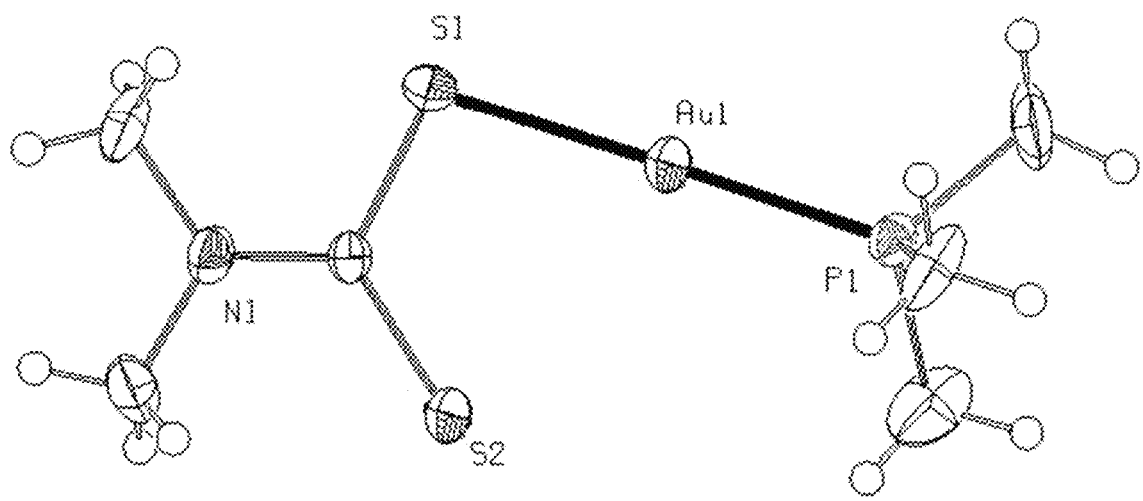
FIG. 1 is a view of the molecular structure of mononuclear complex 1, with partial atom labelling scheme and displacement ellipsoids drawn at 50% probability level.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, "compound" and "complex" are used interchangeably, and are intended to refer to a chemical entity, whether in the solid, liquid or gaseous phase, and whether in a crude mixture or purified and isolated.

Platinum-containing anti-cancer agents, such as cisplatin, can bring about several undesirable side effects in patients. Therefore, researchers have been studying anti-cancer agents which do not contain platinum. Among the emerging class of non-platinum antitumor agents, gold(I) complexes have recently gained attention because of their strong toxicity toward malignant cells, which is generally accompanied by non-cisplatin-like pharmacodynamic and pharmacokinetic properties and mechanisms of action (Tiekink, T. R. E. Anicancer Potential of gold complexes. *Inflammopharmacology*. 2008, 16, 138-142; and Ott, I. On the medicinal chemistry of gold complexes as anticancer drugs. *Coord. Chem. Rev.* 2009, 253, 1670-1681, each incorporated herein by reference in their entirety). The incorporation of a gold metal center into drug scaffolds offers vast potential for creating promising metal-based drug candidates with significant cytostatic and/or cytotoxic effects against various cancer cell lines (Ronconi, L.; Giovagnini, L.; Marzano, C.; Bettio, F.; Graziani, R.; Pilloni. G.; Fregona, D. *Inorg. Chem.* 2005, 44, 1867-1881; and Tiekink, T. R. E. Gold compounds in medicine: potential anti-tumor agents. *Gold Bull.* 2003, 36, 117-124, each incorporated herein by reference in their entirety). The antirheumatic drug, auranofin, and a number of its analogs have shown significant in vitro and in vivo cytotoxic activity (Messori, L.; Abbate, F.; Marcon, G.; Orioli, P.; Fontani, M.; Mini, E.; Mazzei, T.; Carotti, S.; O'Connell, T.; Zanello, P. Gold(III) complexes as potential antitumor agents: solution chemistry and cytotoxic properties of some selected gold(III) compounds. *J. Med. Chem.* 2000, 43, 3541-3548, incorporated herein by reference in its entirety).

Therefore, the first aspect of the disclosure relates to a gold(I) complex represented by formula (I):

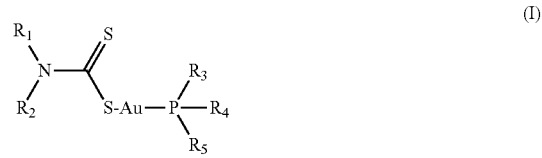

a salt thereof, a solvate thereof, or a combination thereof, where $R_1$ and $R_2$ are independently selected from the group consisting of H, an unsubstituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted arylolefin, an optionally substituted $C_4$-$C_{10}$ alkenyl, and an optionally substituted vinyl;

$R_3$, $R_4$, and $R_5$ are independently selected from the group consisting of H, an optionally substituted $C_1$-$C_3$ alkyl, an optionally substituted $C_3$-$C_5$ cycloalkyl, an optionally substituted cycloalkylalkyl, an optionally substituted arylalkyl, an optionally substituted heteroaryl, an optionally substituted aryl, an optionally substituted heterocyclyl, an optionally substituted arylolefin, an optionally substituted vinyl, an optionally substituted alkylamino, an optionally substituted arylamino, an optionally substituted alkylarylamino, an optionally substituted alkoxy, and an optionally substituted aryloxy; and with the proviso that $R_1$, $R_2$, $R_3$, $R_4$, and $R_5$ are not each an ethyl.

In some embodiments, $R_1$ and $R_2$ are the same unsubstituted alkyl group, and $R_3$, $R_4$, and $R_5$ are the same optionally substituted $C_1$-$C_3$ alkyl group. In other embodiments, $R_1$ and $R_2$ may be methyls, and $R_3$, $R_4$, and $R_5$ are methyls, ethyls, or isopropyls. In one embodiment, $R_1$ and $R_2$ may be are ethyls, and $R_3$, $R_4$, and $R_5$ are methyls. In one embodiment, when $R_3$, $R_4$, and $R_5$ are ethyls, $R_1$ and $R_2$ are not propyls.

The dithiocarbamate ligand may coordinate to the gold(I) ion in a monodentate fashion (as shown in formula (I)), or in a bidentate fashion with both sulfurs chelating the gold(I) ion. Preferably, the dithiocarbamate coordinates to the gold (I) ion in a monodentate fashion.

The term "solvate" means a physical association of the gold(I) complex of formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or non-stoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "pharmaceutically acceptable salt" refers to a protonated form of the gold(I) complex of formula (I) (e.g. an embodiment of the gold(I) complex of formula (I) with a basic substituent, such as an optionally substituted amino group, on $R_1$, $R_2$, or both) with a counter-ion. As used herein, the term "counter-ion" refers to an anion, preferably a pharmaceutically acceptable anion that is associated with the protonated form of the gold(I) complex of formula (I). Non-limiting examples of pharmaceutically acceptable counter-ions include halides, such as fluoride, chloride, bromide, iodide, nitrate, sulfate, phosphate, amide, methanesulfonate, ethanesulfonate, p-toluenesulfonate, salicylate, malate, maleate, succinate, tartrate, citrate, acetate, perchlorate, trifluoromethanesulfonate (triflate), acetylacetonate, hexafluorophosphate, and hexafluoroacetylacetonate. In some embodiments, the counter-ion is a halide, preferably chloride.

The phrase "pharmaceutically acceptable" as used herein refers to counter-ions, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the composition refers to the combination of an active ingredient with a carrier, inert or active, making the composition especially suitable for diagnostic or therapeutic use in vivo or ex vivo.

The term "alkyl", as used herein, unless otherwise specified, refers to a straight, or branched hydrocarbon fragment. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl. As used herein, the term "cyclic hydrocarbon" or "cycloalkyl" refers to a cyclized alkyl group. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as exemplary 1-methylcyclopropyl and 2-methycyclopropyl groups, are included in the definition of cycloalkyl as used in the present disclosure. The $C_1$-$C_3$ alkyl groups include methyl, ethyl, and propyl.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, l-hexenyl, 2-hexenyl, 3-hexenyl, 4-hexenyl, and 5-hexenyl. Exemplary $C_4$-$C_{10}$ alkenyl groups include, without limitation, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl. The $C_4$-$C_{10}$ alkenyl groups do not include allyl.

The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

As used herein, the term "substituted" refers to at least one hydrogen atom that is replaced with a non-hydrogen group, provided that normal valencies are maintained and that the substitution results in a stable compound. When a compound or a R group (denoted as $R_1$, $R_2$, and so forth) is noted as "optionally substituted", the substituents are selected from the exemplary group including, but not limited to, aroyl (as defined hereinafter), halogen (e.g. chlorine, bromine, fluorine or iodine), alkoxy (i.e. straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy), cycloalkyloxy including cyclopentyloxy, cyclohexyloxy, and cycloheptyloxy, aryloxy including phenoxy and phenoxy substituted with halo, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl), hydrocarbyl, arylalkyl, hydroxy, alkoxy, oxo, alkanoyl, alkanoyloxy, amino, alkylamino, arylamino, arylalkylamino, disubstituted amines (e.g. in which the two amino substituents are selected from the exemplary group including, but not limited to, alkyl, aryl, or arylalkyl), alkanylamino, arylamino, alkanoylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —$SO_2NH_2$), substituted sulfonamide, nitro, cyano, carboxy, carbamyl (e.g. —$CONH_2$, —CONHalkyl, —CONHaryl, —CONHarylalkyl or cases where there are two substituents on one nitrogen from alkyl, aryl, or arylalkyl), alkoxycarbonyl, aryl, guanidine, heteroarylcarbonyl, heterocyclyl, and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

As used herein, the term "unsubstituted alkyl" refers to an alkyl group which may be linear or branched and does not have any hydrogen atom that is replaced with a non-hydrogen group. Exemplary unsubstituted alkyl group includes, without limitation, methyl, ethyl, propyl, isopropyl, butyl, tert-butyl, sec-butyl, isobutyl, pentyl, and hexyl.

The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl, and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has one or more oxygen atoms bonded to the ring (i.e. as ring atoms). Preferably, said atom which is bonded to the ring selected from nitrogen or sulfur. An example of a heterocyclyl substituted with one or more oxygen atoms is 1,1-dioxido-1,3-thiazolidinyl.

The term "alkylthio" as used in this disclosure refers to a divalent sulfur with alkyl occupying one of the valencies and includes the groups methylthio, ethylthio, propylthio, butylthio, pentylthio, hexylthio, and octylthio.

The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl.

Examples of aroyl are benzoyl and naphthoyl, and "substituted aroyl" may refer to benzoyl or naphthoyl substituted by at least one substituent including those selected from halogen, amino, nitro, hydroxy, alkyl, alkoxy and haloalkyl on the benzene or naphthalene ring.

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl.

Vinyl refers to an unsaturated substituent having at least one unsaturated double bond and having the formula $CH_2=CH-$. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl.

The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

The gold(I) complex of the first aspect may be prepared by mixing a gold(I) precursor with a dithiocarbamate salt. The gold(I) precursor may be represented by the following formula:

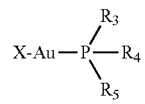

where X is fluoro, chloro, bromo, or iodo.

Exemplary gold(I) precursors include, without limitation, chloro(triethylphosphine)-gold(I), chloro(trimethylphosphine)gold(I), chloro[diphenyl(o-tolyl)phosphine]gold(I), chloro[tri(o-tolyl)phosphine]gold(I), chloro(methyldiphenylphosphine)gold(I), chloro[2-(dicyclohexylphosphino)-biphenyl]gold(I), chloro[2-di-tert-butyl(2',4',6'-triisopropyl-biphenyl)phosphine] gold(I), chloro[di(1-adamantyl)-2-dimethylaminophenylphosphine]gold(I), chloro(2-dicyclohexyl-phosphino-2'-dimethylaminobiphenyl)gold(I), chloro(trimethylphosphite)gold(I), chloro[(1,1'-biphenyl-2-yl)di-tert-butylphosphine]gold(I), chloro[2-dicyclohexyl(2',4',6'-trisopropyl-biphenyl)phosphine]gold(I), chloro[tris(2,3,4,5,6-pentafluorophenyl)-phosphine]gold(I), chloro[tri(p-tolyl)phosphine]gold(I), chloro[2-dicyclohexyl(2',6'-dimethoxybiphenyl)-phosphine] gold(I), chloro[2-dicyclohexyl(2',6';-diisopropoxybiphenyl)-phosphine] gold (I), chloro[2-dicyclohexylphosphino-2',6'-bis(N,N-dimethylamino)-biphenyl]gold(I), chloro {4-[2-di(1-adamantyl)phosphino]phenylmorpholine}gold(I), chloro(2-di-tert-butylphosphino-3,6-dimethoxy-2',4',6'-triisopropylbiphenyl)gold(I), chloro[2-(dicyclohexylphosphino)-3,6-dimethoxy-2',4',6'-triisopropyl-1,1'-biphenyl]gold(I), chloro(2-{bis[3,5-bis(trifluoromethyl)-phenyl]phosphino}-3,6-dimethoxy-2',4',6'-triisopropyl-1,1'-biphenyl)gold(I), and chloro(2-di-tert-butylphosphino-3,4,5,6-tetramethyl-2',4',6'-triisopropylbiphenyl)gold(I).

The dithiocarbamate salt may be represented by the following formula:

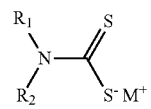

where $M^+$ is an alkali metal cation (e.g. sodium, potassium, cesium, lithium, and rubidium), ammonium, an optionally substituted alkylammonium, an optionally substituted arylammonium, or an optionally substituted alkylarylammonium.

Exemplary dithiocarbamate salts include, without limitation, sodium dimethyldithiocarbamate, potassium dimethyldithiocarbamate, sodium diethyldithiocarbamate, and potassium diethyldithiocarbamate.

The dithiocarbamate salt may be dissolved in a solvent to give a solution with a concentration in a range of 0.01-1 M, preferably 0.01-0.5 M, more preferably 0.05-0.2 M. A volume of the solvent may be in a range of 1-50 ml, preferably 1-20 ml, more preferably 1-10 ml. The gold(I) precursor may be suspended in the solvent to give a suspension with a concentration in a range of 0.01-0.5 M, preferably 0.01-0.2 M, more preferably 0.01-0.1 M. A volume of the solvent may be in a range of 5-100 ml, preferably 5-50 ml, more preferably 10-30 ml. The suspension may be cooled to a temperature in a range of −10 to 10° C., preferably −5 to 5° C. under an inert atmosphere provided by nitrogen gas, argon gas, helium gas, or combinations thereof. The suspension may be cooled with an external cooling source such as an ice bath with or without salt, or a thermostatted thermocirculator. The dithiocarbamate salt solution can be added to the suspension dropwise, and then stirred for about 1-24 hours, preferably 1-10 hours, more preferably 1-5 hours. The reaction may be shaken/stirred throughout the duration of the reaction by employing a rotary shaker, a magnetic stirrer, or an overhead stirrer. In another embodiment, the reaction mixture is left to stand (i.e. not stirred). In one embodiment, the reaction mixture is preferably mixed in a centrifugal mixer with a rotational speed of at least 500 rpm, preferably at least 800 rpm, more preferably at least 1,000 rpm, even though it can also be mixed with a spatula. In one embodiment, the reaction mixture is sonicated.

The reaction mixture may be then filtered to remove insoluble material. The solvent may be evaporated to give the crude gold(I) complex. The gold(I) complex may be purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase. A preferred method includes extraction with organic solvents, but is not limited to those exemplified. The yield of the gold(I) complex is at least 50%, preferably at least 75%, more preferably at least 80%.

As used herein, the term "solvent" includes, but is not limited to, water (e.g. tap water, distilled water, doubly distilled water, deionized water, deionized distilled water), organic solvents, such as ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, $\alpha,\alpha,\alpha$,-trifluoromethylbenzene, fluorobenzene), chlorinated solvents (e.g. chlorobenzene, dichloromethane, 1,2-dichloroethane, 1,1-dichloroethane, chloroform), ester solvents (e.g. ethyl acetate, propyl acetate), amide solvents (e.g. dimethylformamide, dimethylacetamide, N-methyl-2-pyrrolidone), urea solvents, ketones (e.g. acetone, butanone), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, and mixtures thereof. Preferably, the solvent is methanol.

The second aspect of the disclosure relates to a composition comprising the gold(I) complex of the first aspect, the salt thereof, the solvate thereof, or a combination thereof, and a pharmaceutically acceptable carrier or excipient.

As used herein, a "composition" refers to a mixture of the active ingredient with other chemical components, such as pharmaceutically acceptable carriers and excipients.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

As used herein, "derivative" refers to a chemically or biologically modified version of a chemical compound that is structurally similar to a parent compound and (actually or theoretically) derivable from that parent compound. A "derivative" differs from an "analog" in that a parent compound may be the starting material to generate a "derivative", whereas the parent compound may not necessarily be used as the starting material to generate an "analog". A derivative may or may not have different chemical or physical properties of the parent compound. For example, the derivative may be more hydrophilic or it may have altered reactivity compared to the parent compound. Derivatization (i.e. modification) may involve substitution of one or more moieties within the molecule (e.g. a change in functional group). The term "derivative" also includes conjugates, and prodrugs of a parent compound (i.e. chemically modified derivatives which can be converted into the original compound under physiological conditions).

As used herein, the term "analog" refers to a chemical compound that is structurally similar to a parent compound, but differs slightly in composition (e.g. at least one atom or functional group is different, added, or removed). The analog may or may not have different chemical or physical properties than the original compound and may or may not have improved biological and/or chemical activity. For example, the analog may be more hydrophilic or it may have altered reactivity compared to the parent compound. The analog may mimic the chemical and/or biological activity of the parent compound (i.e. it may have similar or identical activity), or, in some cases, may have increased or decreased activity. The analog may be a naturally or non-naturally occurring variant of the original compound. Other types of analogs include isomers (enantiomers, diastereomers, and the like) and other types of chiral variants of a compound, as well as structural isomers.

As used herein, a "binder" holds the ingredients in a tablet together. Binders ensure that tablets and granules can be formed with required mechanical strength, and give volume to low active dose tablets. Binders may be: (1) saccharides and their derivatives, such as sucrose, lactose, starches, cellulose or modified cellulose such as microcrystalline cellulose, carboxymethyl cellulose, and cellulose ethers such as hydroxypropyl cellulose (HPC), and sugar alcohols such as xylitol, sorbitol or maltitol, (2) proteins such as gelatin, and (3) synthetic polymers including polyvinylpyrrolidone (PVP), polyethylene glycol (PEG). Binders are classified according to their application. Solution binders are dissolved in a solvent (for example water or alcohol can be used in wet granulation processes). Examples include gelatin, cellulose, cellulose derivatives, polyvinylpyrrolidone, starch, sucrose, and polyethylene glycol. Dry binders are added to the powder blend, either after a wet granulation step, or as part of a direct powder compression (DC) formula. Examples include cellulose, methyl cellulose, polyvinylpyrrolidone, and polyethylene glycol.

The term "active ingredient", as used herein, refers to an ingredient in the composition that is biologically active, for example, the gold(I) complex of formula (I), a salt thereof, and a solvate thereof.

In most embodiments, the composition comprises at least 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the gold(I) complex, the pharmaceutically acceptable salt thereof, the pharmaceutically acceptable solvate thereof, or a combination thereof. The composition may comprise 0.01-50 µM, 0.01-30 µM, preferably 0.01-10 µM of the gold(I) complex, relative to the total composition. In some embodiments, the composition comprises up to 0.1 wt %, 1 wt %, 5 wt %, or 10 wt % of the pharmaceutically acceptable salt thereof. In some embodiments, the composition comprises up to 0.1 wt %, 1 wt %, 5 wt %, or 10 wt % of the pharmaceutically acceptable solvate thereof. Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

In one embodiment, the composition is used for treating cancer and further comprises a second active ingredient, such as a chemotherapeutic agent, for the treatment or prevention of neoplasm, of tumor or cancer cell division, growth, proliferation and/or metastasis in the subject; induction of death or apoptosis of tumor and/or cancer cells; and/or any other form of proliferative disorder.

Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifamib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab. The composition may comprise 0.1-50 wt % of the second active ingredient, preferably 10-40 wt %, more preferably 10-20 wt %, relative to the weight of the first active ingredient.

The third aspect of the disclosure relates to a method for treating cancer, comprising administering the composition of the second aspect to a subject in need thereof.

As used herein, the terms "treat", "treatment", and "treating" in the context of the administration of a therapy to a subject in need thereof refer to the reduction or inhibition of the progression and/or duration of a disease, the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The terms "patient", "subject", and "individual" are used interchangeably. As used herein, they refer to individuals suffering from a disease and encompass mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In preferred embodiments, the subject is a human.

A subject in need of treatment includes a subject already with the disease, a subject which does not yet experience or exhibit symptoms of the disease, and a subject predisposed to the disease. In preferred embodiments, the subject is a person who is predisposed to cancer, e.g. a person with a family history of cancer. White women or a person with (i) certain inherited genes (e.g. mutated BRCA1, BRCA2, ATM, TP53, CHEK2, PTEN, CDH1, STK11, and PALB2), (ii) radiation to one's chest, and/or (iii) exposure to diethylstilbestrol (DES), are at a higher risk of contracting breast cancer.

Dithiocarbamates are bidentate S,S'-chelating ligands that possess an extraordinary ability to form stable coordination complexes with metal ions due to the "chelation effect". Therefore, dithiocarbamate units tethered to gold(I) phosphine motifs may be able to prevent dissociation of the metal ion and interactions of the metal ion with sulfur-containing proteins, thereby reducing renal toxicity (Bodenner, D. L.; Dedon, P. C.; Keng, D. C.; Borch, R. F. Effect of diethyldithiocarbamate on cis-diaminedichloroplatinum(II)-induced cytotoxicity, DNA cross linking, and γ-glutamyl transpeptidase inhibition. *Cancer Res.* 1986, 4, 2745-2750; and Fregona, D.; Giovagnini, L.; Ronconi, L.: Marzano, C.; Trevisan, A.; Sitran, S.; Biondi, B.; Bordin, F. Pt(II) and Pd(II) derivatives of tributylsarcosinedithiocarbamate: Synthesis, chemical and biological characterization and in vitro nephrotoxicity. *J. Inorg. Biochem.* 2003, 93, 181-189, each incorporated herein by reference in their entirety).

Thus, in at least one embodiment, the subject refers to a cancer patient with an existing renal disease. Examples of renal disease include, without limitation, autosomal dominant polycystic kidney disease, autosomal recessive polycystic kidney disease, acute pre-renal kidney failure, acute intrinsic kidney failure, chronic pre-renal kidney failure, chronic intrinsic kidney failure, and chronic post-renal kidney failure.

In another embodiment, the subject refers to a cancer patient who have been previously administered/treated with cisplatin and have cisplatin resistance (for example in the form of high ERCC1 mRNA levels, overexpression of HER-2/neu, activation of the PI3-K/Akt pathway, loss of p53 function, and/or overexpression of antiapoptotic bcl-2).

The neoplastic activity of the tumor or cancer cells may be localized or initiated in one or more of the following: blood, brain, bladder, lung, cervix, ovary, colon, rectum, pancreas, skin, prostate gland, stomach, intestine, breast, liver, spleen, kidney, head, neck, testicle, bone (including bone marrow), thyroid gland, and central nervous system. Preferably, the composition may be used to treat breast cancer. In some embodiments, the composition is used to treat cisplatin-resistant breast cancer.

In treating certain cancers, the best approach is a combination of surgery, radiotherapy, and/or chemotherapy. Therefore, in at least one embodiment, the composition is employed with radiotherapy. In another embodiment, the composition is employed with surgery. The radiotherapy and/or surgery may be before or after the composition is administered.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%. 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include but are not limited to CT scan, MRI, DCE-MRI and PET scan.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the gold(I) complex of formula (I), the salt thereof, the solvate thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. In at least one embodiment, the gold(I) complex of formula (I), the salt thereof, the solvate thereof, or the combination thereof is administered in an effective amount in a range of 1-100 mg/kg based on the weight of the subject, preferably 10-80 mg/kg, more preferably 20-50 mg/kg.

One purpose of a composition is to facilitate administration of the gold(I) complex of formula (I), the salt thereof, the solvate thereof, and a combination thereof to a subject. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The composition thereof may be administered in a single dose or multiple individual divided doses. In some embodiments, the composition is administered at various dosages (e.g. a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety).

In one embodiment, the $IC_{50}$ is in a range of 0.01-100 µM, preferably 0.01-80 µM, more preferably 0.04-70 µM. As used herein, the term "$IC_{50}$" refers to a concentration of the gold(I) complex of formula (I), the salt thereof, or the solvate thereof, which causes the death of 50% of cancer cells in 72 hours (3 days).

The $IC_{50}$ can be determined by standard cell viability assays, such as, without limitation, ATP test, Calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. In a preferred embodiment, a XTT assay is used.

In at least one embodiment, the human cancer cells are derived from commercial cell lines, including but are not limited to HeLa cervical cancer cells, A549 lung cancer cells, HCT15 colon cancer cells, HCT8 or HRT8 colon cancer cells, HCT116 colon cancer cells, DLD1 colon cancer cells, MCF7 breast cancer cells, MDA-MB231 breast cancer cells, A2780 ovarian cancer cells, HePG2 liver cancer cells, and DU145 prostatic cancer cells. In some embodiments, cisplatin-resistant cancer cells are used. These cells may be cultured with low doses of cisplatin in order to build resistance to cisplatin while maintaining cell viability. Examples of cisplatin-resistant cancer cells include, but are not limited to, A2780-cis cisplatin-resistant ovarian cancer cells and SGC7901-cis cisplatin-resistant gastrointestinal cancer cells. In other embodiments, the human cancer cells are cancer cells of a human patient who has been diagnosed with, is suspected of having, or is susceptible to or at risk of having at least one form of cancer, preferably breast cancer.

In most embodiments, the method further comprises measuring a concentration of a biomarker and/or detecting a mutation in a biomarker before and/or after the composition is administered. As used herein, the term "biomarker" refers to a characteristic that is objectively measured and evaluated as an indicator of normal biological processes, pathogenic processes or pharmacological responses to a therapeutic intervention. Exemplary cancer biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Specifically, potentially predictive cancer biomarkers include, without limitation, mutations in genes BRCA1 and BRCA2 for breast cancer. Cancer biomarkers may be useful in determining the aggressiveness of an identified cancer as well as its likelihood of responding to the treatment. Examples of such prognostic biomarkers include, without limitation, elevated expression of estrogen receptor (ER) and/or progesterone receptor (PR), which are associated with better overall survival in patients with breast cancer.

The mutation in the biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art.

The concentration of the biomarker may be measured with an assay, for example an antibody-based method (e.g. an ELISA).

As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like.

Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used.

The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term "sample" includes any biological sample taken from the subject including a cell, tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor.

In some embodiments, the concentration of the biomarker is measured before and after the administration. When the concentration of the biomarker is maintained, the method may further comprise increasing the effective amount of the gold(I) complex of formula (I), the salt thereof, the solvate thereof, or the combination thereof by at least 5%, at least 10%, or at least 30%, up to 50%, up to 60%, or up to 80% of an initial effective amount that is in a range of 1-100 mg/kg based on the weight of the subject. The increased effective amount may be in a range of 1.05-180 mg/kg, preferably 15-140 mg/kg, more preferably 25-90 mg/kg. The subject may be administered with the increased dosage for a longer period (e.g. 1 week more, 2 weeks more, or 2 months more) than the duration with the initial effective amount.

In some embodiments, the mutation in the biomarker is detected before administrating the composition to identify subjects predisposed to the disease. For example, women with a BRCA1 germline mutation are at a higher risk of contracting breast and ovarian cancer.

In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Having generally described this disclosure, a further understanding can be obtained by reference to certain specific examples which are provided herein for purposes of illustration only and are not intended to be limiting unless otherwise specified.

EXAMPLE 1

Materials and Methods

Ethidium bromide (EB), sodium N,N-dimethyldithiocarbamate hydrate (DMDT), and sodium N,N-diethyldithiocarbamate hydrate (DEDT) were purchased from Sigma-Aldrich. Tris-(hydroxymethyl)aminomethane (Tris buffer) (Merck), adenosine-5'-monophosphate disodium salt (5'-AMP), cytidine-5'-monophosphate disodium salt hydrate (5'-CMP), guanosine-5'-monophosphate disodium salt (5'-GMP), thymine-5'-monophosphate (5'-TMP), and $CH_3OH$ were obtained from Fluka Chemicals Co. and were stored at −20° C. Disodium salt of CT-DNA (calf thymus DNA) was purchased from Sigma Chem. Co. and was stored at 4° C. All reagents as well as solvents were used as received. Human breast cancer cell lines, MDA-MB231 and MCF7, were provided by American Type Culture Collection (ATCC). Cells were cultured in Dulbecco's Modified Eagle Medium (DMEM) supplemented with 10% fetal calf serum (FCS), penicillin (100 kU $L^{-1}$) and streptomycin (0.1 g $L^{-1}$) at 37° C. in a 5% $CO_2$-95% air atmosphere. MTT (3-(4,5-dimethylthiazol-2-yl)-2,5-diphenyltetrazolium bromide), a yellow tetrazole, was purchased from Sigma Chemical Co, St. Louis, Mo., USA.

EXAMPLE 2

Synthesis of Therapeutic Gold(I) Complexes

Following the previous studies on mixed phosphine gold (I) dithiocarbamate compounds with antitumor activity and in continuation of the interest in the synthesis of gold(I) complexes to better understand the chemical and physical behavior of biologically relevant dithiocarmato(phosphine)gold(I) complexes, gold(I) complexes 1-5 were synthesized and fully characterized by elemental analysis, FTIR, NMR measurements and UV-Vis spectroscopic techniques (Altaf, M.; Monim-ul-Mehboob, M.; Seliman, A. A.; Sohail, M.; Wazeer, I. M.; Isab, A. A.; Li, L.; Dhuna, V.; Bhatia, G.; Dhuna, K. Synthesis, Characterization and anticancer activity of gold(I) complexes that contain tri-teri-butylphosphine and dialkyldithiocarbamate ligands. Eur. J. Med. Chem. 2015, 95, 464-472; and Altaf, M.; Monim-ul-Mehboob, M.; Isab, A. A.; Bhatia, G.; Dhuna, K.; Altuwaijri, S. The synthesis, spectroscopic characterization and anticancer activity of new mono and binuclear phosphinegold(I) dithiocarbamate complexes. New J. Chem. 2015, 39, 377-385, each incorporated herein by reference in their entirety).

Mixed ligands gold(I) complexes (dithiocarbamato(phosphane)gold(I)) 1-5 were synthesized according to a method similar to the synthesis reported in the literature (Al-Sa'ady, K.; McAuliffe, A. C.; Parish, V. R.; Sandbank, A. J. A General Synthesis for Gold(I) Complexes. Inorg. Synth. 1985, 23, 191-194, incorporated herein by reference in its entirety).

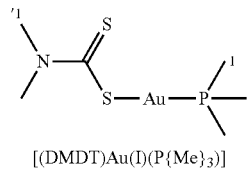

[(DMDT)Au(I)(P{Me}$_3$)]      (1)

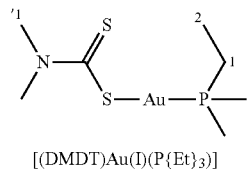

[(DMDT)Au(I)(P{Et}$_3$)]      (2)

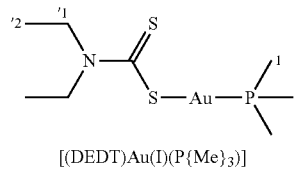

[(DEDT)Au(I)(P{Me}$_3$)]      (3)

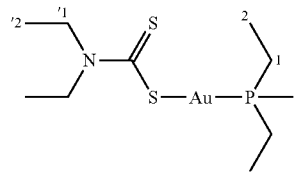

[(DEDT)Au(I)(P{Et}$_3$)]      (4)

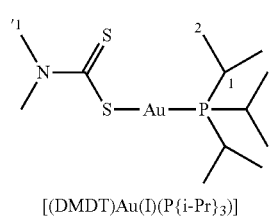

[(DMDT)Au(I)(P{i-Pr}$_3$)]      (5)

To a stirred suspension of chlorotrialkyl(phosphine)gold (I) (0.50 mmol) in methanol (20 ml), cooled at 0° C. in an ice-bath under atmospheric nitrogen gas flow, a solution of sodium dimethyldithiocarbamate (DMDT) or sodium diethyldithiocarbamate (DEDT) (0.50 mmol) in 5 ml of methanol was added dropwise. Rapidly, the solid was dissolved and the resulting yellow or orange solution was stirred for about 2 h. Then, the solution was filtered to remove insoluble materials. Evaporation of methanol at room temperature afforded a yellow or orange solid which was dissolved in diethyl ether (10 ml). To remove the byproduct, sodium chloride, the organic layer was washed with water and extracted, dried with anhydrous $Na_2SO_4$ and filtered. Complete removal of the solvent afforded gold(I) complexes 1-5 as a yellow or orange solid. The gold(I) complex was dried under reduced pressure at room temperature overnight over $P_2O_5$. The yield of the compounds 1-5 was in the range of 81-86%. Elemental analysis for complexes is presented in Table 1. The complexes prepared in the present disclosure were characterized by their physical properties, UV-Vis spectroscopy NMR, IR, elemental analysis, and X-ray crystallography. The density functional calculations (DFC) studies based hybrid B3LYP was also performed to optimize the structures of gold(I) complex 1. All the data support the formation of the desired complexes 1-5.

TABLE 1

Elemental analysis of gold(I) complexes 1-5

| Complex | Found (Calculated) % | | | |
|---|---|---|---|---|
| | % C | % H | % N | % S |
| (Me)$_3$PAu(S$_2$CN{Me}$_2$) (1) | 18.26(18.32) | 3.86(3.84) | 3.48(3.56) | 16.23(16.32) |
| (Et)$_3$PAu(S$_2$CN{Me}$_2$) (2) | 24.75(24.83) | 4.90(4.86) | 3.18(3.22) | 14.76(14.73) |
| (Me)$_3$PAu(S$_2$CN{Et}$_2$) (3) | 22.65(22.81) | 4.59(4.55) | 3.30(3.32) | 15.17(15.22) |
| (Et)$_3$PAu(S$_2$CN{Et}$_2$) (4) | 28.43(28.51) | 4.51(5.44) | 2.98(3.02) | 13.61(13.84) |
| (i-Pr)$_3$PAu(S$_2$CN{Me}$_2$) (5) | 30.01(30.19) | 5.74(5.70) | 2.88(2.93) | 13.32(13.43) |

EXAMPLE 3

Electronic Spectra

Electronic spectra were obtained for the gold(I) complexes using Lambda 200, Perkin-Elmer UV-Vis spectrometer. UV-Vis spectroscopy was used to determine the stability of the complexes in DMSO. Electronic spectra were recorded on freshly prepared samples of each complex in a buffer at room temperature. The resulting UV-Vis absorption data are shown in Table 2.

TABLE 2

$\lambda_{max}$ values derived from UV-Vis spectra for Au(I) complexes 1-5

| Complex | $\lambda_{max}$ (nm) |
|---|---|
| (Me)$_3$PAu(S$_2$CN{Me}$_2$) (1) | 270, 321 |
| (Et)$_3$PAu(S$_2$CN{Me}$_2$) (2) | 270, 320 |
| (Me)$_3$PAu(S$_2$CN{Et}$_2$) (3) | 270, 321 |
| (Et)$_3$PAu(S$_2$CN{Et}$_2$) (4) | 272, 333 |
| (i-Pr)$_3$PAu(S$_2$CN{Me}$_2$) (5) | 270, 322 |

The optical electronic absorption spectra show a similar pattern for all of the complexes. The gold(I) complexes 1-5 absorbed intensely at two regions, 270-272 nm and 321-333 nm, which were attributed to the intramolecular intraligand transition corresponding to π→π* in the NCS and CSS moieties, respectively (Yang, Y.; Zuo, B.; Li, J.; G. Chen, G. Studies on the stability of four-membered ring chelates Part V. The stability of dialkyl dithiocarbamate chelates. *Spectrachim. Acta Part A.* 1996, 52 1915-1919; Liao, Q. Q.; Wang, Y. Z.; Li, J. Y.; Xiang, B.; Cheng, M. R.; Zhang, J. Q. Spectra study of a sodium triethylenetetramine-bisdithiocarbamate and its complexes with heavy metal ions. *Spectrosc. Specir. Anal.* 2009, 29, 829-832; and Jia, Y. Y.; Gao, Y. B.; Lu, L.; Wang, N. X.; Xu, M. X. Flocculation mechanism and oil removal performance of dithiocarbamate. *China Environ. Sci.* 2009, 29, 201-206, each incorporated herein by reference in their entirety). This result indicates that partial double bonds exist in the N—C group, which supports the monodentate complexation of the dithiocarbamate to the gold(I) ion.

EXAMPLE 4

Mid and Far-IR Studies

The IR spectra of the dithiocarbamate ligands and the dithiocarbamato(phosphane)gold(I) complexes were recorded on a Perkin-Elmer FTIR 180 spectrophotometer using KBr pellets over 4000-400 cm$^{-1}$. Far-infrared spectra were recorded for complexes 1-5 as cesium chloride disks at a 4 cm$^{-1}$ resolution at room temperature on a Nicolet 6700 FT-IR with Far-IR beam splitter. The most significant bands recorded in the FTIR spectra of the dithiocarbamate ligand and gold(I) complexes 1-5 are reported in Tables 3 and 4.

TABLE 3

IR frequencies, υ (cm$^{-1}$) for complexes 1-5

| Complex | υ(C—NSS) | $\upsilon_{shift}$ | υ(SC=S) | $\upsilon_{shift}$ | υ(SC—S) | $\upsilon_{shift}$ |
|---|---|---|---|---|---|---|
| NaS$_2$CN{Me}$_2$ | 1487 s | — | 1043 s | — | 963 s | — |
| NaS$_2$CN{Et}$_2$ | 1457 s | — | 1064 s | — | 986 s | — |
| (Me)$_3$PAu(S$_2$CN{Me}$_2$) (1) | 1501 s | 14 | 974 s | −69 | 958 s | −5 |
| (Et)$_3$PAu(S$_2$CN{Me}$_2$) (2) | 1476 s | 19 | 986 s | −78 | 951 s | −35 |
| (Me)$_3$PAu(S$_2$CN{Et}$_2$) (3) | 1492 s | 35 | 996 s | −47 | 973 s | −10 |
| (Et)$_3$PAu(S$_2$CN{Et}$_2$) (4) | 1485 s | 28 | 1002 | −62 | 984 s | −2 |
| (i-Pr)$_3$PAu(S$_2$CN{Me}$_2$) (5) | 1503 s | 16 | 1029 | −14 | 977 s | −9 |

TABLE 4

FT-IR frequencies, υ (cm$^{-1}$) for complexes 1-5

| Compound | υ(Au—S) | υ(Au—P) |
|---|---|---|
| (Me)$_3$PAu(S$_2$CN{Me}$_2$) (1) | 289 | 199 |
| (Et)$_3$PAu(S$_2$CN{Me}$_2$) (2) | 278 | 202 |
| (Me)$_3$PAu(S$_2$CN{Et}$_2$) (3) | 272 | 198 |
| (Et)$_3$PAu(S$_2$CN{Et}$_2$) (4) | 276 | 201 |
| (i-Pr)$_3$PAu(S$_2$CN{Me}$_2$) (5) | 277 | 195 |

The FTIR spectra was analyzed to determine the mode of coordination and to evaluate the nature of bonding in the complexes. In examining the infrared spectra of dithiocarbamate complexes, the three main regions of interest are: (1) 1580-1450 cm$^{-1}$ n due to υ(C—N) stretching vibrations, (2) 1060-940 cm$^{-1}$ due to υ(C—S), and (3) 430-250 cm$^-$n due to the v(M-S) (Ajibadel, A. P.; Idemudial, G. O.; Okoh, I. A. Synthesis, characterization and antibacterial studies of metal complexes of sulfadiazine with n-alkyl-n-phenyldithiocarbamate. *Bull. Chem. Soc. Ethiop.* 2013, 27, 77-84, incorporated herein by reference in its entirety).

The dithiocarbamate compounds 1-5 exhibited a characteristic band in the range 1476-1507 cm$^{-1}$ that was assigned to the N—CSS stretching mode: this band indicates a carbon-nitrogen bond order that is between a single bond (1250-1350 cm$^{-1}$) and a double bond (1640-1690 cm$^{-1}$) (S. Wajda, K. Drabent, Bull. Acad. Polon. Sci., Sci. Chim. 25 (1977) 963; N. Nakamoto, J. Fujita, R. A. Condrote, Y. Morimoto, J. Chem. Phys. 39 (1963) 42; Durgaprasad, G.; Sathyanarayana, N. D.; Patel, C. C. Normal coordinate analysis of dialkyldithiocarbamate and its selenium analogue. *Can. J. Chem.* 1969, 47, 631-635; and Odola, J. A.; Woods, O. A. J. New Nickel(II) Mixed Ligand Complexes of Dithiocarbamates with Schiff Base. *J. Chem. Pharm. Res.* 2011, 3, 865-871, each incorporated herein by reference in their entirety).

In the dithiocarbamate ligands, the bands in the region 1457-1487 cm$^{-1}$ that were assigned to the v(N—CSS) stretching vibrations shifted to higher energies in the range 1460-1501 cm$^{-1}$ upon complexation, thus showing an increase in the carbon-nitrogen double bond character (Herlimger, W. A.; Wenhold, N. S.; Long, V. T. Infrared spectra of amino acids and their metal complexes. II. Geometrical isomerism in bis(amino acidato)copper(II) complexes. *J. Am. Chem. Soc.* 1970, 92, 6474-6481, incorporated herein by reference in its entirety). This shift was caused by increased electron delocalization towards the metal ion upon coordination and confirmed the coordination of the metal ions to the dithiocarbamate ligands. Because these frequency modes lie between the ones associated with single C—N and double C=N bonds, the partial double bond character of the thioureide bond was confirmed for complexes 1-5 (Jian, F.; Wang, Z.; Bai, Z.; You, X.; Fun, H.; Chinnakali, K.; Razak, A. L. The crystal structure, equilibrium and spectroscopic studies of bis(dialkyldithiocarbamate) copper(II) complexes [$Cu_2(R_2dtc)_4$] (dtc=dithiocarbamate). *Polyhedron.* 1999, 18, 3401-3406, incorporated herein by reference in its entirety).

The bands due to the —CSS moiety are usually coupled to other vibrations and are very sensitive to the environment of this group, thereby distinguishing monodentate and bidentate dithiocarbamate coordination. The presence of only one band in the region 940-1060 cm$^{-1}$ was assumed by Bonati and Ugo to indicate a completely symmetrical bonding of the dithiocarbamate ligand, which acted in a bidentate mode (Bonati, F.; Ugo, R. Organotin(IV) N,N-disubstituted dithiocarbamates. *J. Organomet. Chem.* 1967, 10, 257-268, incorporated herein by reference in its entirety). Conversely, a split band indicates a monodentate bound ligand. In the complexes reported here, without wishing to be bound by theory, the presence of two bands in the investigated region suggests the dithiocarbamate is monodentate and exhibited asymmetrical behavior.

The coordination of phosphine, $PR_3$, and dithiocarbamato, S—CN(R)$_2$, to the Au(I) center via phosphorus and sulfur donor atoms and the formation of P—Au—S bonds can be supported by the presence of v(Au—P) and v(Au—S) bands, respectively, in the ranges 272-289 and 195-202 cm$^{-1}$ in far-FTIR.

EXAMPLE 5

Solution NMR Measurements

All NMR measurements were carried out on a Jeol JNM-LA 500 NMR spectrophotometer at 297 K. The $^1$H NMR spectra were recorded at a frequency of 500.00 MHz. The 13C NMR spectra were obtained at a frequency of 125.65 MHz with $^1$H broadband decoupling and referenced to TMS. The spectral conditions were: 32 k data points, 0.967 s acquisition time, 1.00 s pulse delay, and 45° pulse angle. $^{31}$P NMR spectra were measured at a frequency of 202.35 MHz, using 0.269 s acquisition time, 20.00 s pulse delay and 6.20 µs pulse with $^1$H broadband decoupling. $^{31}$P NMR chemical shifts were measured relative to the internal reference 85% $H_3PO_4$. The $^1$H, $^{13}$C, and $^{31}$P NMR chemical shifts are given in Table 5, Table 6, and Table 7, respectively.

TABLE 5

$^1$H NMR chemical shifts of gold(I) precursor and dithiocarbamato(phosphane)gold(I) complexes in CDCl$_3$

| | $^1$H(δ in ppm) | | | | | | |
|---|---|---|---|---|---|---|---|
| Compound | H1 | J(Hz) ($^2J_{PH}$, $J_{HH}$) | H2 | J(Hz) ($^3J_{PH}$) | H1' | J(Hz) $J_{HH}$ | H2' |
| (Me)$_3$PAuCl | 1.63, d | 11.3, — | | | | | |
| (Et)$_3$PAuCl | 1.85, dq | 10.3, 7.7 | 1.21, td | 18.9 | | | |
| (i-Pr)$_3$PAuCl | 2.28, dp | 9.5, 7.3 | 1.31, dd | 23.2 | | | |
| (Me)$_3$PAu(S$_2$CN{Me}$_2$) (1) | 1.61, d | 10.7, — | | | 3.47, s | | |
| (Et)$_3$PAu(S$_2$CN{Me}$_2$) (2) | 1.63, d | 10.7, — | | | 3.90, q | 6.7 | 1.30, t |
| (Me)$_3$PAu(S$_2$CN{Et}$_2$) (3) | 1.84, dq | 9.9, 7.7 | 1.23, td | 18.3 | 3.47, s | | |
| (Et)$_3$PAu(S$_2$CN{Et}$_2$) (4) | 1.85, p | 7.9, 7.9 | 1.22, td | 18.9 | 3.46, q | 6.7 | 1.21, t |
| (i-Pr)$_3$PAu(S$_2$CN{Me}$_2$) (5) | 2.29, dp | 9.4, 7.1 | 1.33, dd | 23.2 | 3.47, s | | | s, singlet; d, doublet; t, triplet; q, quartet; p, pentet; dd, doublet of doublet; dq, doublet of quartet; td, triplet of doublet; dp, doublet of pentet.

TABLE 6

$^{13}$C NMR chemical shifts of gold(I) precursor and the dithiocarbamato(phosphane)gold(I) complexes in CDCl$_3$

| Compound | C=S | C1 | J(Hz) $^1J_{CP}$ | C2 | C1' | C2' |
|---|---|---|---|---|---|---|
| (Me)$_3$PAuCl | — | 16.3, 16.0 | 39.0 | — | — | — |
| (Et)$_3$PAuCl | — | 18.3, 18.0 | 37.4 | 9.0 | | |

TABLE 6-continued $^{13}$C NMR chemical shifts of gold(I) precursor and the dithiocarbamato(phosphane)gold(I) complexes in CDCl$_3$

| Compound | C=S | C1 | J(Hz) $^1J_{CP}$ | C2 | C1' | C2' |
|---|---|---|---|---|---|---|
| (i-Pr)$_3$PAuCl | — | 24.1, 23.8 | 31.1 | 20.3 | — | — |
| (Me)$_3$PAu(S$_2$CN{Me}$_2$) (1) | 207 | 16.6, 16.3 | 36.3 | — | 45.2 | — |
| (Et)$_3$PAu(S$_2$CN{Me}$_2$) (2) | 206 | 16.4, 16.1 | 37.3 | — | 48.9 | 11.9 |
| (Me)$_3$PAu(S$_2$CN{Et}$_2$) (3) | 208 | 18.4, 18.2 | 34.2 | 8.8 | 45.0 | — |
| (Et)$_3$PAu(S$_2$CN{Et}$_2$) (4) | 206 | 18.4, 18.2 | 33.2 | 8.7 | 48.9 | 12.0 |
| (i-Pr)$_3$PAu(S$_2$CN{Me}$_2$) (5) | 208 | 23.9, 23.7 | 28.9 | 20.1 | 45.0 | — |

TABLE 7

$^{31}$P NMR chemical shifts of gold(I) precursor and the dithiocarbamato(phosphane)gold(I) complexes in CDCl$_3$

| Compound | P | $\delta_{shift}$ |
|---|---|---|
| (Me)$_3$PAuCl | −11 | |
| (Me)$_3$PAu(S$_2$CN{Me}$_2$) (1) | −8.7 | 2.3 |
| (Et)$_3$PAu(S$_2$CN{Me}$_2$) (2) | −8.8 | 2.2 |
| (Et)$_3$PAuCl | 29.4 | |
| (Me)$_3$PAu(S$_2$CN{Et}$_2$) (3) | 31.9 | 2.5 |
| (Et)$_3$PAu(S$_2$CN{Et}$_2$) (4) | 32.2 | 2.8 |
| (i-Pr)$_3$PAu(I)Cl | −36.7 | |
| (i-Pr)$_3$PAu(S$_2$CN{Me}$_2$) (5) | −35.1 | 1.6 |

TABLE 8

$^{13}$C Solid state NMR chemical shifts of dithiocarbamato(phosphane)gold(I) complexes

| Compound | C=S | C1 | C2 | C1' | C2' |
|---|---|---|---|---|---|
| NaS$_2$CN{Me}$_2$ | 208 | | | 47.1 | |
| NaS$_2$CN{Et}$_2$ | 206 | | | 48.3 | 12.9 |
| (Et)$_3$PAu(I)Cl | | 17.0 | 9.8 | | |
| (Me)$_3$PAu(S$_2$CN{Me}$_2$) (1) | 209 | 20.1 | — | 48.9 | — |
| (Et)$_3$PAu(S$_2$CN{Me}$_2$) (2) | 209 | 20.0 | — | 49.8 | 16.7 |
| (Me)$_3$PAu(S$_2$CN{Et}$_2$) (3) | 211 | 23.4 | 14.2 | 49.2 | — |
| (Et)$_3$PAu(S$_2$CN{Et}$_2$) (4) | 211 | 22.6 | 15.2 | 52.0 | 15.6 |

Figure 4:
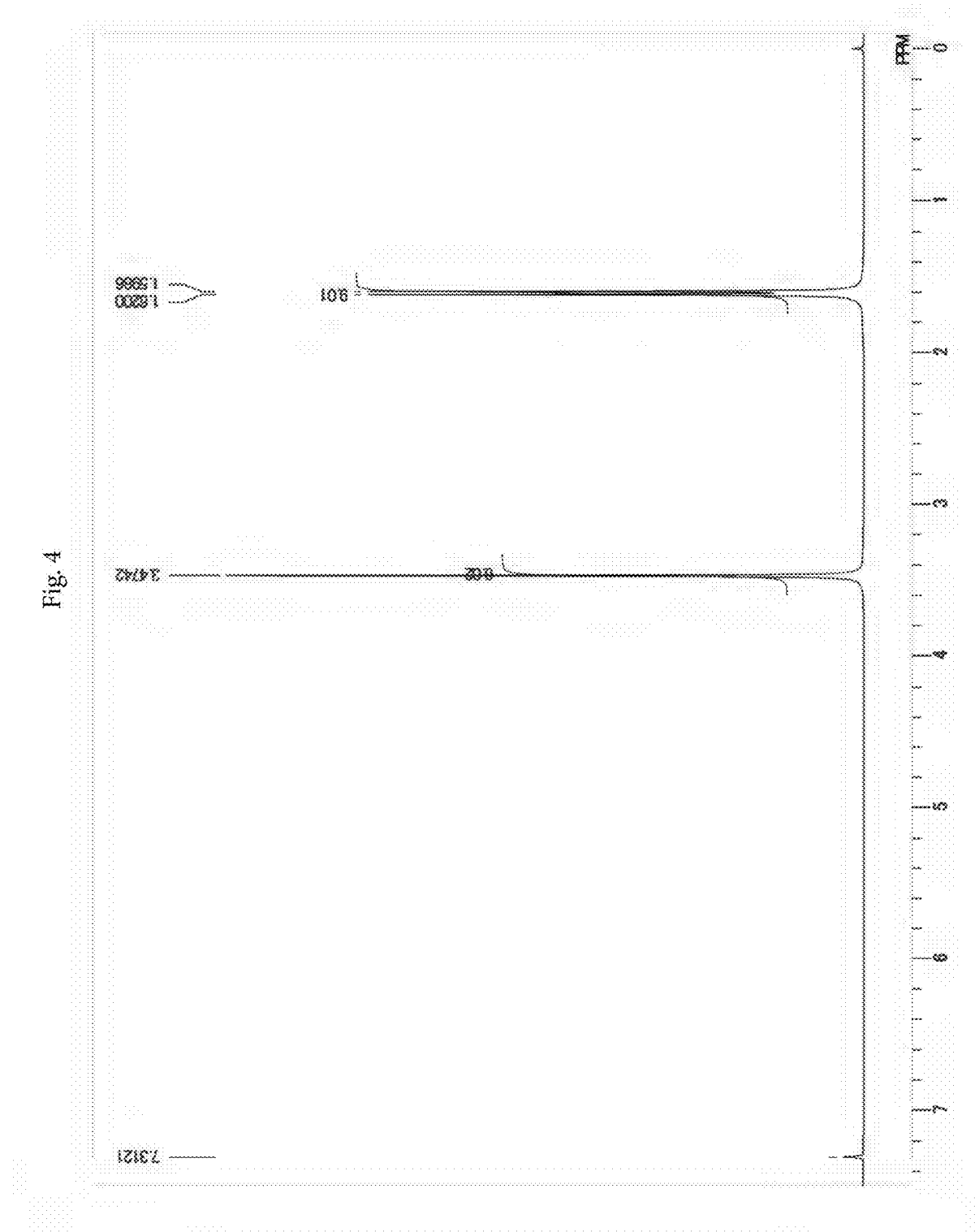
FIG. 4 is a $^1$H solution state NMR spectrum of complex 1 taken at 500 MHz in $CDCl_3$.
Figure 5:
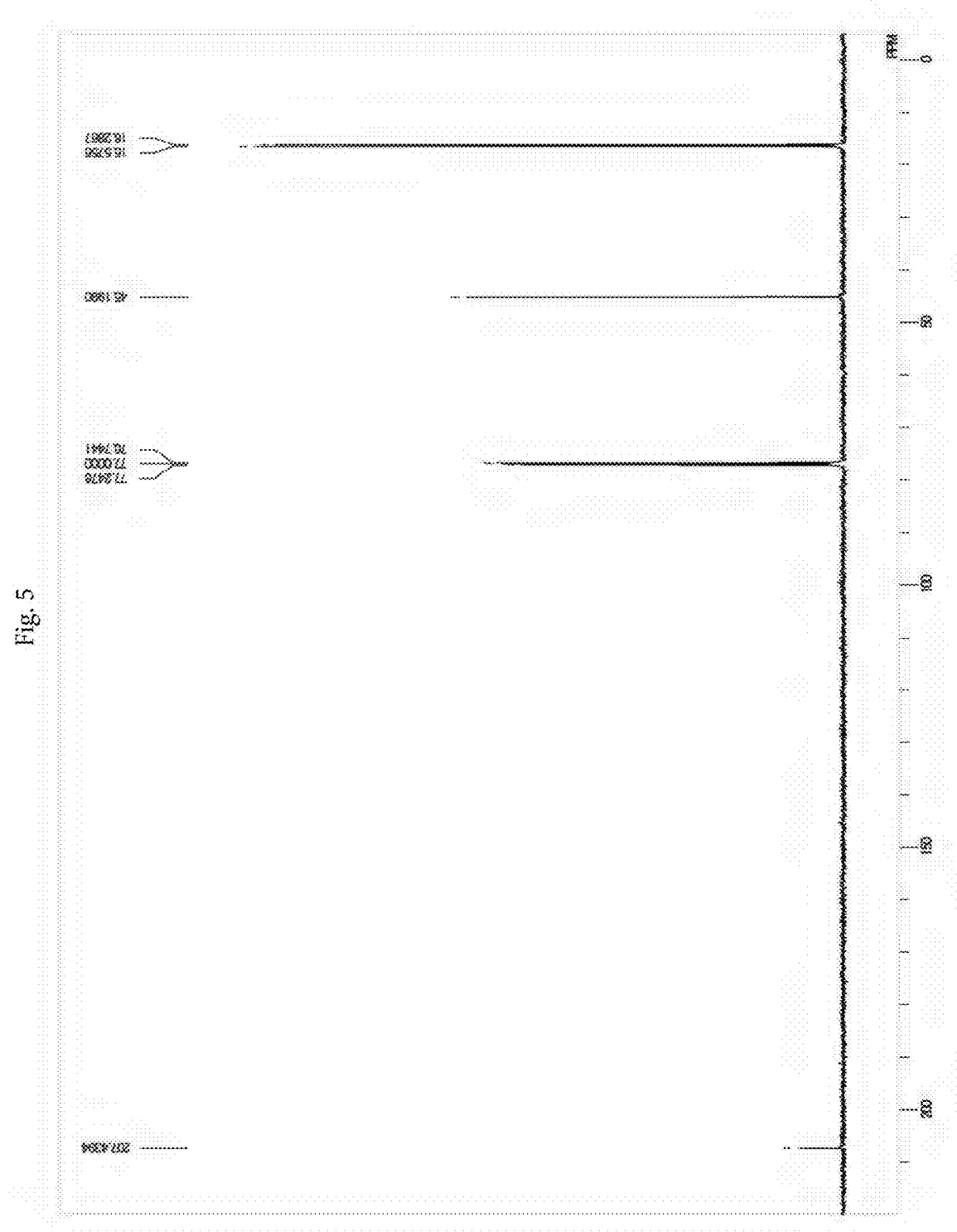
FIG. 5 is a $^{13}C\{^1H\}$ solution state NMR spectrum of complex 1 taken at 125.65 MHz in $CDCl_3$.

The $^1$H NMR data, especially the integral of the signals of the protons of the phosphine and dithiocarbamate groups, supports the structures of the synthesized complexes. For instance, the $^1$H NMR spectrum (FIG. 4) of complex 1 displayed a doublet at 1.61 ppm, due to the methyl proton of the trimethylphosphine, and a singlet at 3.47 ppm, corresponding to the methyl groups of the S$_2$CN(CH$_3$)$_2$ ligands, with a relative integration 9:6, as expected for the proposed stoichiometry. The $^{13}$C NMR spectrum shown in FIG. 5 confirms the structure of complex 1. A complete list of $^1$H and $^{13}$C NMR data of compounds 1-5 and the corresponding gold(I) precursors is given in Tables 5 and 6, respectively. For the alkyl groups bound to the phosphine moiety in the complexes 1-5, the $^1$H and $^{13}$C NMR signals are very close for the gold(I) precursors. There was no significant change in the $^2J_{P-H}$ coupling constant for the gold(I) precursors and their corresponding dithiocarbamato(phosphane)gold(I) complexes. However, the P—C coupling constant, $^1J_{P-C}$, showed a reduction of 2.2-4.2 Hz upon complexation. The $^{31}$P{$^1$H}-NMR data (Table 7) of the complexes 1-5 show singlet resonances which are shifted by ca. 1.6 to 2.8 ppm to higher field compared to those of the gold(I) precursors.

EXAMPLE 6

Solid State NMR Studies

The $^{13}$C solid-state NMR spectra were acquired on a Bruker 400 MHz spectrometer at ambient temperature of 25° C. Samples were packed into 4 mm zirconium oxide rotors. Cross polarization and high power decoupling were employed. Pulse delay of 7.0 s and a contact time of 5.0 ms were used in the CPMAS experiments. The magic angle spinning rates were 4 and 8 kHz. Carbon chemical shifts were referenced to TMS by setting the high frequency isotropic peak of solid adamantane to 38.56 ppm. The solid NMR data is given in Table 8.

At the spinning rate of 4 kHz, the isotropic signals for all complexes were observed for the carbon atom in NCS$_2$ fragment of the dithiocarbamate ligand, indicating the anisotropy that could take place due to the sp$^2$ hybridization of these atoms. Complexes 1-4 showed significant downfield shifts (~4 ppm) for all carbons bonded to sulfur and phosphorus atoms in the dithiocarbamate and phosphine ligands, respectively, with respect to the free ligands and the gold(I) precursor. This observation can be attributed to the strong electron donation by the S atom of the dimethyldithiocarbamate and the P atom of trimethylphosphine. Compared to the chemical shifts in solution NMR, significant de-shielding in the solid state was observed. The solid state and solution NMR chemical shifts for complexes 1-4 are similar, indicating the stability of the complexes in solid state.

EXAMPLE 7

X-ray Diffraction Analysis

Figure 2:
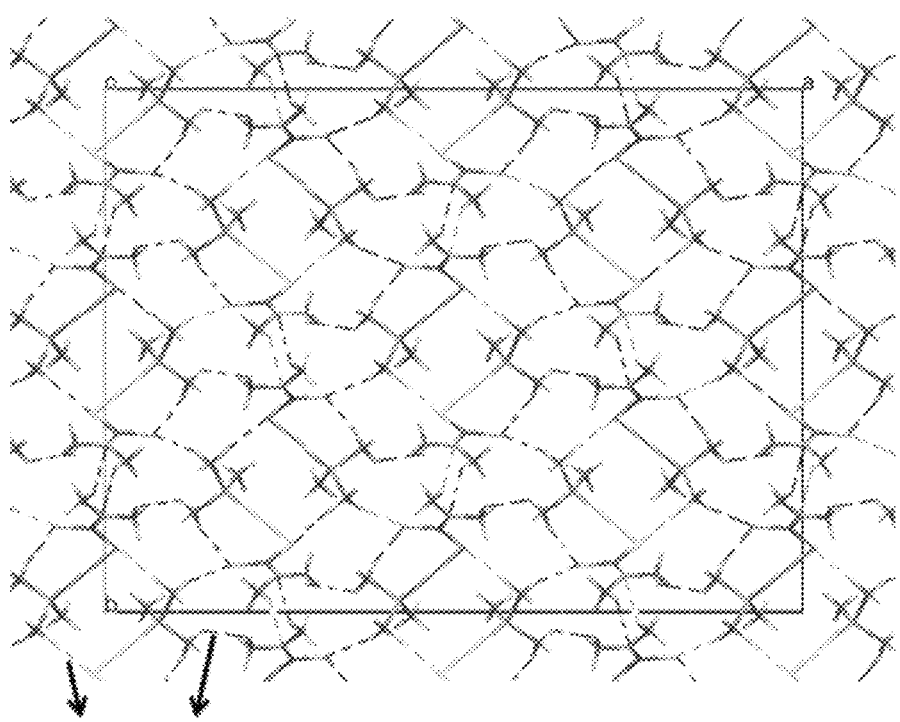
FIG. 2 is a view of the crystal packing diagram of complex 1 along plane containing the c axis of the unit cell, with the dotted lines showing short contacts between different functional groups of molecules.

Single crystal data collection for complex 1 was performed at 173K (−100° C.) on a Stoe Mark II-IPD System equipped with a two-circle goniometer and using MoK$_\alpha$ graphite monochromatic radiation (Sheldrick, M. G. A short history of SHELX. *Acta Cryst.* 2008, A64, 112-122, incorporated herein by reference in its entirety). Diffraction data for 1 was collected using ω rotation scans of 0-180° at φ=0° and of 0-180° at φ=90° with step Δω=1.0°, exposures of 1 minute per image, 2θ range=2.29-59.53° and d$_{min}$−d$_{max}$=17.779-0.716 Å. The distance between the imaging plate and the sample was 100 mm, and the structure was solved by direct methods using the program SHELXS-97 (Stoe, Cie, X-Area V1.35 and X-RED32 V1.31 Software, Stoe and Cie GmbH, Darmstadt. Germany. 2006, incorporated herein by reference in its entirety). The refinement and all further calculations were carried out using SHELXL-97. The H-atoms were either located from Fourier difference maps and freely refined or included in calculated positions and treated as riding atoms using SHELXL default parameters. The non-H atoms were refined anisotropically, using weighted full-matrix least-squares on $F^2$. Empirical or multi-scan absorption corrections were applied using MULS-CANABS routines in PLATON (Sheldrick, M. G. A short history of SHELX. *Acta Cryst.* 2008, A64, 112-122, incorporated herein by reference in its entirety). A summary of crystal data and refinement details for compound 1 are given in Table 9. FIGS. 1 and 2 were drawn using the programs PLATON and MERCURY (Macrae, F. C.; Edgington, R. P.; McCabe, P.; Pidcock, E.; Shields, P. G.; Taylor, R.; Towler, M.; Van de Streek, J. Mercury: visualization and analysis crystal structures. *J. Appl. Cryst.* 2006, 39, 453-457, incorporated herein by reference in its entirety). Selected bond-distances and bond angles are given in Table 10.

TABLE 9

Summary of crystal data and details of
the structure refinement for complex 1

| Complex | 1 |
|---|---|
| CCDC No. | 1006138 |
| Empirical formula | $C_6H_{15}Au_1N_1P_1S_2$ |
| Formula weight | 393.27 |
| Crystal size/mm | 0.15 × 0.3 × 0.09 |
| Wavelength/Å | 0.71073 |
| Temperature/K | 173 (2) |
| Crystal symmetry | Orthorhombic |
| Space group | Fdd2 |
| a/Å | 32.075 (2) |
| b/Å | 24.0898 (14) |
| c/Å | 6.1700 (3) |
| V/Å$^3$ | 4767.4 (5) |
| Z | 8 |
| $D_c$/Mg m$^{-3}$ | 2.192 |
| μ(Mo—Kα)/mm$^{-1}$ | 12.78 |
| F(000) | 2944 |
| θ Limits/° | 2.1-25.7 |
| Collected reflections | 8135 |
| Unique reflections($R_{int}$) | 2123 (0.082) |
| Observed reflections[$F_o > 2\sigma(F_o)$] | 2175 |
| Goodness of fit on $F^2$ | 1.08 |
| $R_1(F)$, $^a[I > 2\sigma(I)]$ | 0.043 |
| $wR_2$ ($F^2$), $^b[I > 2\sigma(I)]$ | 0.120 |
| Largest diff. peak, hole/e Å$^{-3}$ | 1.40, −3.10 |

TABLE 10

Selected bond distances and bond angles for complex 1

| Bond Length (Å) | Found [Calc.] | Bond Angles (°) | Found [Calc.] |
|---|---|---|---|
| Au—P1 | 2.249 (3)[2.396] | P1—Au—S1 | 176.88 (13) [178.3] |
| Au—S1 | 2.326 (3) [2.453] | C1—P1—C2 | 103.7 (10) [104.0] |
| P1—C1 | 1.775 (16) [1.881] | C1—P1—C3 | 104.1 (9) [104.1] |
| P1—C2 | 1.792 (14) [1.881] | C2—P1—C3 | 105.0 (8) [104.2] |
| P1—C3 | 1.797 (15) [1.879] | C1—P1—Au | 117.5 (6) [116.3] |
| S1—C4 | 1.758 (12) [1.826] | C2—P1—Au | 113.1 (6) [112.3] |

Figure 3:
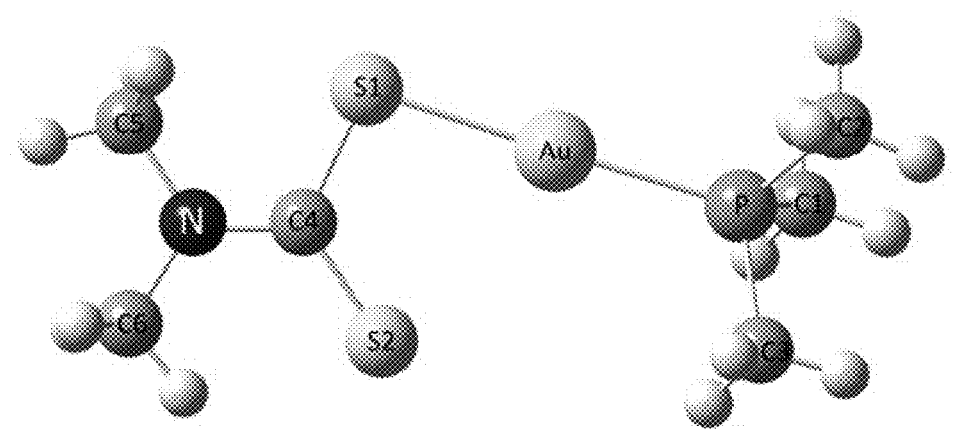
FIG. 3 shows an optimized geometry of complex 1, obtained at the B3LYP/LanL2DZ level of theory using GAUSSIAN09 W.

The X-ray molecular structure of [(Me)$_3$PAu (S$_2$CN{Me}$_2$)] (1) is shown in FIG. 1. In this structure, gold(I) is coordinated to the P donor atom of trimethylphosphine and the S donor atom of dimethyldithiocarbamate. The Au—S and Au—P bond distances were 2.326 (3) and 2.249 (3) Å respectively. The Au—P and Au—S bond distances were comparable with the [Et$_3$PAu(S$_2$CNEt$_2$)] complex (Ho, Y. S.; Tiekink, T. R. E. Z. *Kristallogr. NCS.* 2005, 220, 342-344, incorporated herein by reference in its entirety). The geometry around the Au(I) metal atom is linear and similar to other Au(I) complexes (Sänger, I.; Lerner, -W. H.; Sinke, T.; Bolte, M. Iodido(tri-tert-butylphosphane-κP)gold (I) *ActaCryst.* 2012, E68, m708; Lu, P.; Boorman, C. T.; Slawin, Z. M. A.; Larrosa, I. Gold(I)-mediated C—H—Activation of Arenes. *J. Am. Chem. Soc.* 2010, 132, 5580-5581; Marsh, E. R. The space groups of point group C$_3$: some corrections, some comments. *Acta Cryst.* 2002, B58, 893-899: and Schmidbaur, H.; Brachthiuser, B.; Steigelmann, O.; Beruda, H. Preparation and Structure of Hexakis [(trialkylphosphane)aurio(I)]methanium(2+) Salts [(LAu)$_6$ C]$^{2+}$(X$^-$)$_2$ with L=Et$_3$P, iPr$_3$P and X=BF$_4^-$, B$_3$O$_3$F$_4^-$. *Chem. Ber.* 1992, 125, 2705-2710, each incorporated herein by reference in their entirety). In [(Me)$_3$PAu(S$_2$CN(Me)$_2$)] (1), the S—Au—P bond angle was 176.88 (13). The S—Au—P bond angle value showed considerable deviation from an ideal linear angle of 180° (Table 10) and confirmed the presence of distorted linear geometry in this molecule. The interactions between different functional groups of the molecules resulted in a three-dimensional network shown in FIG. 2. The optimized structure of the compound 1 obtained from the B3LYP/LANL2DZ level of calculations is shown in FIG. 3. Table 10 presents a good agreement between the experimental and calculated structural parameters for almost all bond distances and angles, which supports the crystallographic data.

EXAMPLE 8

Computational Study

The structures of the [(Me)$_3$PAu(DMDT)] complex was optimized without any geometrical constrains using GAUSSIAN09 program (Frisch, J. M.; Trucks, W. G.; Schlegel, B. H.; Scuseria, E. G.; Robb, A. M.; Cheeseman, J. R.; Scalmani, G.; Barone, V.; Mennucci, B.; Petersson, A. G.; Nakatsuji, H.; Caricato, M.; Li, X.; Hratchian, P. H.; Izmaylov, F. A.; Bloino, J.; Zheng, G.; Sonnenberg, L. J.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, A. J.; Peralta, E. J. Jr.; Ogliaro, F.; Bearpark, M.; Heyd, J. J.; Brothers, E.; Kudin, N. K.; Staroverov, N. V.; Kobayashi, R.; Normand, J.; Raghavachari, K.; Rendell, A.; Burant, C. J.; Iyengar, S. S.; Tomasi, J.; Cossi, M.; Rega, N.: Millam, M. J.; Klene, M.; Knox, E. J.; Cross, B. J.; Bakken, V.; Adamo, C.; Jaramillo, J.; Gomperts, R.; Stratmann, E. R.; Yazyev, O.; Austin, A. J.; Cammi, R.; Pomelli, C.; Ochterski, W. J.; Martin, L. R.; Morokuma, K.; Zakrzewski, G. V.; Voth, A. G.; Salvador, P.; Dannenberg, J. J.; Dapprich, S.; Daniels, D. S.; Farkas, Ö.; Foresman, B. J.; Ortiz, V. J.; Cioslowski, J.; Fox, J. D. Gaussian 09, Revision A.1, Gaussian, Inc. *Wallingford CT.* 2009, incorporated herein by reference in its entirety). The hybrid B3LYP density functional (the three-parameter Becke functional with correlation from the Lee-Yang-Parr functional) with the Los Alamos National Laboratory-2 double-ζ (LANL2DZ) basis set was employed (Becke, D. A. Density-functional exchange-energy approximation with correct asymptotic behavior. *Phys. Rev.* 1988, 38, 3098; Lee, C. W.; Yang, W. D; Parr. G. R. Development of the Colle-Salvetti correlation-energy formula into a functional of the electron density. *Phys. Rev.* 1988, B37, 785; Hay, J. P.; Wadt, R. W. Ab initio effective core potentials for molecular calculations. Potentials for the transition metal atoms Sc to Hg. *J. Chem. Phys.* 1985, 82, 270; Wadt, R. W.; Hay, J. P. Ab initio effective core potentials for molecular calculations. Potentials for main group elements Na to Bi. *J. Chem. Phys.* 1985, 82, 284; and Hay, J. P.; Wadt, R. W. Ab initio effective core potentials for molecular calculations. Potentials for K to Au including the outermost core orbitals. *J. Chem. Phys.* 1985, 82, 299, each incorporated herein by reference in their entirety). The calculated data was consistent with the experimental data. Moreover, stationary points were confirmed by frequency calculations. Calculated bond distances and angles are listed alongside with experimental values in Table 10 for compound 1.

EXAMPLE 9

Cell Cultures

Human breast cancer cells (MDA-MB231, MCF-7) were grown in Dulbecco's modified Eagle's medium (DMEM) supplemented with 10% fetal bovine serum (FBS) and 1% penicillin (10,000 units) with streptomycin (10 mg) in a 74 cm$^2$ flask and incubated until 80% confluence was obtained in a humidified environment of 5% $CO_2$-95% air at 37° C.

EXAMPLE 10

MTT Assays for Anticancer Activity of Gold(I) Complexes 1-5

Cancer cells were seeded and maintained in quadruplicate in a 96-well tissue culture plate at 5×10$^3$ cells per well in 150 µl of the same medium. The cancer cells were incubated for 24 hours before the treatment. All compounds were dissolved in 50% DMSO. Therefore, DMSO was used as a negative control. Complexes 1-5 and cisplatin (positive control) at 0.01 µM, 0.05 µM, 0.1 µM, 1 µM, 5 µM, 10 µM, and 50 µM concentrations were prepared in DMEM. The final DMSO concentration, in each well, was less than 0.1%.

The cancer cells were treated with the synthesized compounds 1-5 and cisplatin and then incubated for 24 h. The medium from the wells was discarded and 100 µL of DMEM containing MTT (3-(4,5-dimethylthiazol-2-yl)-2,5-diphenyltetrazolium bromide) (5 mg/mL) was added to the wells. The cells were incubated in a $CO_2$ incubator at 37° C. in the dark for 4 h. After incubation, a purple colored formazan (an artificial chromogenic dye, a product of the reduction of water insoluble tetrazolium salts, such as MTT, by dehydrogenases and reductases) was produced by the cells and appeared as dark crystals in the bottom of the wells. The medium from each well was discarded carefully to avoid disruption of the monolayer. 100 µL of isopropanol was added in each well. The solution was thoroughly mixed in the wells to dissolve the formazan crystals which ultimately results into a purple solution. The absorbance of the 96-well plate was taken at 570 nm with Mithras$^2$LB943 against a blank (e.g. unreduced MTT in isopropanol). All data presented are mean t standard deviation.

Figure 6:
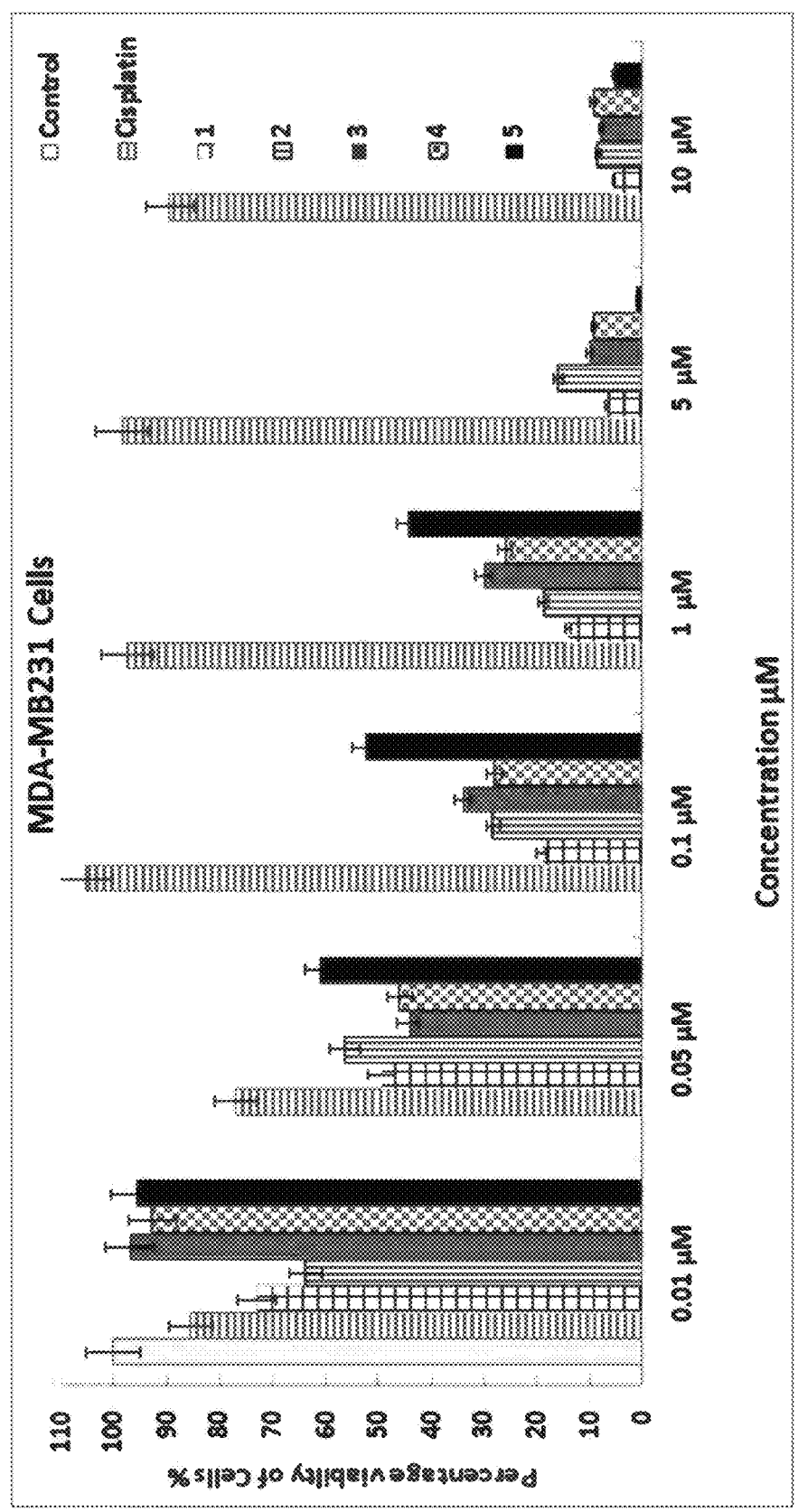
FIG. 6 shows the cytotoxicity of compounds 1-5 to MDA-MB231 cells.
Figure 7:
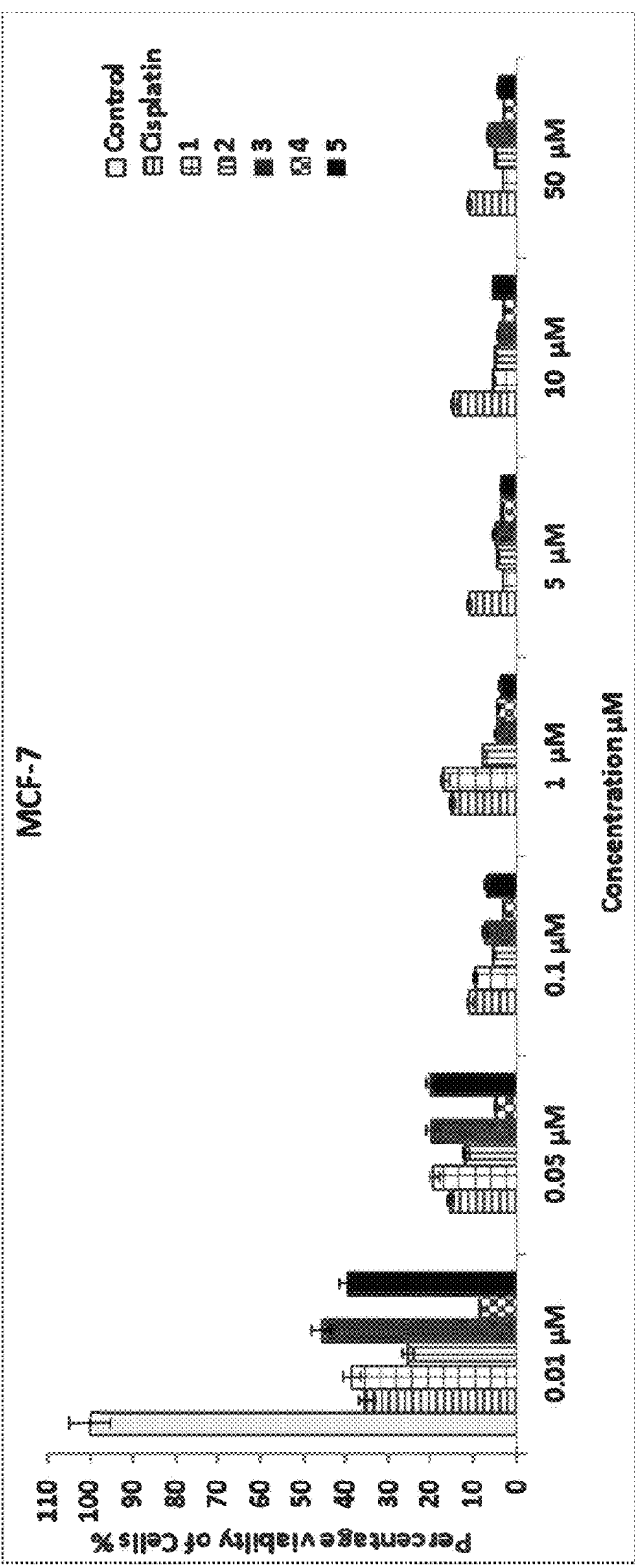
FIG. 7 shows the cytotoxicity of compounds 1-5 to MCF-7 cells.
Figures 8I, 8J:
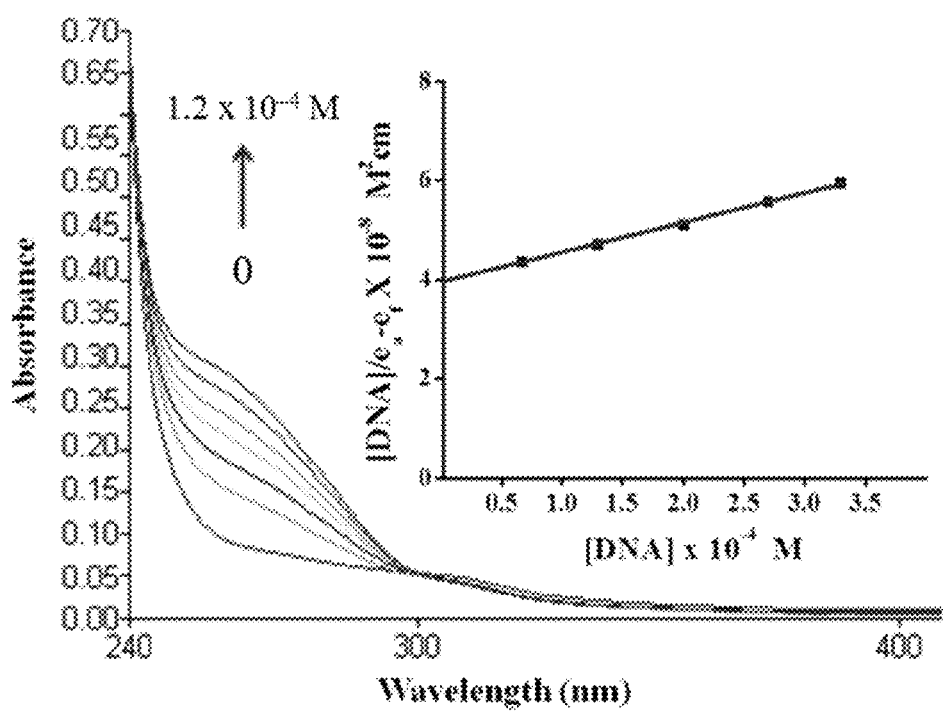
FIG. 8I is an overlay of the absorption spectra of complex 5 in the absence and presence of CT DNA.
FIG. 8J is a plot of $[DNA]/(e_a-e_f)$ against [DNA] for the titration of CT DNA with complex 5.

The concentration-dependent antiproliferative effects of complexes 1-5 after 24 hours of incubation against a fixed number of human cancer cells are shown in FIGS. 6 and 7. The results were consistent with the expectation that the cell inhibition was augmented with increasing concentrations of the complexes 1-5 for both MDA-MB231 and MCF-7 cancer cells respectively. It is generally observed from FIGS. 6 and 7 that the concentration-dependent antiproliferative effect of complexes 1-5 was stronger in MCF-7 cancer cells than in MDA-MB231 cancer cells. In the concentration-dependent cell growth inhibition study, at all concentrations (0.01-10 µM), complexes 1-5 showed much better cell inhibition against the MDA-MB231 cancer cell line than cisplatin, as shown in FIG. 6. Furthermore, compounds 1-5 and cisplatin demonstrated comparable cell inhibition against the MCF-7 cancer cell line, as shown in FIG. 7.

The exact antiproliferation mechanisms of dithiocarbamato(phosphane)gold(I) type complexes on cancer cell lines remain vague. The significantly diminished renal toxicity of [(DACH)Au(pn)]Cl$_3$ ("DACH" refers to 1,2-diaminocyclohexane, and "pn" refers to propylene diamine) complex could be attributed to the different antiproliferative mechanism of action and selective sparing of the proximal tubular epithelial cells (Ahmed, A.; Al Tamimi, M. D.; Isab, A. A.; Alkhawajah, M. M. A.; Shawarby, A. M. Histological Changes in Kidney and Liver of Rats Due to Gold(III) Compound [Au(en)Cl$_2$]Cl. *PLoS ONE*. 2012, 7, e51889, incorporated herein by reference in its entirety). In addition, most gold compounds display a reduced affinity for DNA, and it seems reasonable that DNA is neither the primary nor the exclusive target for most gold complexes. Recent studies have proposed a different mode of action for these compounds: in most cases, induced apoptosis was the mode of cell death (Vivek, S.; Kyoungweon, P.; Mohan, S. Colloidal dispersion of gold nanorods: Historical background, optical properties, seed-mediated synthesis, shape separation and self-assembly. *Materials Science and Engineering*. 2009. R65, 1-38; Niemeyer, M. C. Nanoparticles, Proteins, and Nucleic Acids: Biotechnology Meets Materials Science. *Angew. Chem. Intl. Ed.* 2001, 40, 4128-4158; and Pellegrino, T.; Kudera, S.; Liedl, T.; Javier, M. A.; Manna, L.; Parak, J. W. On the Development of Colloidal Nanoparticles towards Multifunctional Structures and their Possible Use for Biological Applications. *Small*. 2005, 1, 48-63, each incorporated herein by reference in their entirety). The mechanism for inducing apoptosis is not precisely delineated. The mechanisms associated with the inhibitory effects of complexes 1-5 on the proliferation of rapidly dividing cancer cells may consist of a cumulative impact on the induction of cell cycle blockage, interruption of the cell mitotic cycle, apoptosis (programmed cell death), and necrosis (premature cell death) (Taatjes, J. D.; Sobel, E. B.; Budd, C. R. Morphological and cytochemical determination of cell death by apoptosis. *Histochem Cell Biol*. 2008, 129, 33-43; Takemura, G.; Kanoh, M.; Minatoguchi, S. M.; Fujiwara, H. Cardiomyocyte apoptosis in the failing heart—A critical review from definition and classification of cell death. *Intel. J. Cardio*. 2013, 167, 2373-2386; and Hayashi, R.; Nakatsui, K.; Sugiyama, D.; Kitajima, T.; Oohara, N.; Sugiya, M.; Osada, S.; Kodama, H. Antitumor activities of Au(I) complexed with bisphosphines in HL-60 cells. *J. Inorg. Biochem*. 2014, 137, 109-114, each incorporated herein by reference in their entirety).

The in vitro cytotoxic effect of mixed ligand gold(I) complexes 1-5 against MDA-MB231 and MCF-7 were studied using the MTT assay. The in vitro cytotoxic activity depends on the exposure time and the concentrations of the complexes. For that reason, different concentrations of the complexes and a 3-day exposure protocol to determine the $IC_{50}$ values for all five complexes and cisplatin were used.

The $IC_{50}$ data for the Au(I) complexes 1-5 is in a range of 0.043-0.055 µM for MDA-MB231 cells (Table 11). For theses MDA-MB231 cancer cells, the order of in vitro cytotoxicity is complex 3 (0.043 µM)>complex 1 (0.044 µM), complex 4 (0.044 µM)>complex 2 (0.055 µM)>complex 5 (0.70 µM)>cisplatin (25.8 µM). All of the complexes showed significant cytotoxic effects against the breast cancer cell line MDA-MB231 and were found to be more active than cisplatin to a large extent, specifically 37- to 600-fold more cytotoxic than cisplatin. The complexes could also overcome both intrinsic and acquired resistance to cisplatin.

TABLE 11

IC$_{50}$ (µM) of Cisplatin and compounds 1-5

| Complexes | IC$_{50}$ (µM) | |
|---|---|---|
| | MDA | MCF-7 |
| (Me)$_3$PAu(S$_2$CN{Me}$_2$) (1) | 0.044 ± 0.001 | 0.0078 ± 0.0002 |
| (Et)$_3$PAu(S$_2$CN{Me}$_2$) (2) | 0.055 ± 0.001 | 0.0064 ± 0.0002 |
| (Me)$_3$PAu(S$_2$CN{Et}$_2$) (3) | 0.043 ± 0.001 | 0.0088 ± 0.0003 |
| (Et)$_3$PAu(S$_2$CN{Et}$_2$) (4) | 0.044 ± 0.001 | 0.0053 ± 0.0002 |
| (i-Pr)$_3$PAu(S$_2$CN{Me}$_2$) (5) | 0.70 ± 0.019 | 0.0079 ± 0.0002 |
| Cisplatin | 25.8 ± 0.71 | 0.0059 ± 0.0002 |

The IC$_{50}$ data for the Au(I) complexes 1-5 is in the range of 0.0053-0.88 µM for MCF-7 cells (Table 11). It is apparent from the IC$_{50}$ data for MCF-7 cancer cells that complexes 1-5 showed comparable in vitro cytotoxicity to cisplatin. Complex 4 was a better cytotoxic agent than complexes 1, 2, 3, and 5 for MCF-7 cancer cells, as the order of in vitro cytotoxicity in terms of IC$_{50}$ values is complex 4 (0.0053 µM)>cisplatin (0.0059 µM)>complex 2 (0.0064 µM)>complex 1 (0.0078 µM)>complex 5 (0.0078 µM)>complex 3 (0.0088 µM).

In general, the anticancer activity of the synthesized complexes 1-5 against the MDA-MB231 and MCF-7R breast human cancer cell lines was interesting and these complexes exhibited better anticancer activity than in other gold compounds in the literature (Barreiro, E.; Casas, S J.; Couce, D. M.; Sanchez, A.; Sordo, J.; Vázquez-López, M. E. J Inorg. Heteronuclear gold(I)-silver(I) sulfanylcarboxylates: Synthesis, structure and cytotoxic activity against cancer cell lines. *J. Inorg. Biochem.* 2014, 131, 68-75; Kivekäs, R.; Colacio, E.; Ruiz, J.; López-González, D. J.; León, P. Bromopalladates(II) of Xanthine Derivatives. Crystal Structure of 1,3,8-Trimethylxanthinium Tribromopalladate(II) Monohydrate. *Inorg Chim Acta.* 1989, 159, 103-110; Ortego, L.; Cardoso, F.; Martins, S.; Fillat, F. M.; Laguna, A.; M. Meireles, M.; Villacampa, D. M.; Gimeno, C. M. Strong inhibition of thioredoxin reductase by highly cytotoxic gold(I) complexes. DNA binding studies. *J. Inorg. Biochem.* 2014, 130, 32-37; and Ott, I. Koch, T.; Shorafa, H.; Bai, Z.; Poeckel, D.; Steinhilber, D.; Gust, R. Synthesis, cytotoxicity, cellular uptake and influence on eicosanoid metabolism of cobalt alkyne modified fructoses in comparison to auranofin and the cytotoxic COX inhibitor Co-ASS. *Org. Biomol. Chem.* 2005, 3, 2282-2286, each incorporated herein by reference in their entirety).

EXAMPLE 11

DNA Binding

Gold(I) complexes, beginning with auranofin, are gaining attention as a new class of chemotherapeutics because of their strong tumor cell growth-inhibiting effect (Nobili, S.; Mini, E.; Landini, I.; Gabbiani, C.; Casini, A.; Messori, L. Gold Compounds as Anticancer Agents: Chemistry, Cellular Pharmacology, and Preclinical Studies. *Med. Chem. Res.* 2010, 30, 550-580, incorporated herein by reference in its entirety). Because DNA is the potential intracellular target for many anticancer drugs due to its predominant role in controlling cellular functions, the metallodrug-DNA interaction is significant because of its ability to function as a rational design system for the development of new efficient drugs that target DNA. DNA interaction can be achieved through intercalation between the metal complex and DNA, which results in hypochromism with or without a red/blue shift, and/or through non-intercalative/electrostatic interaction, which causes hypochromism (Liu, Z. C.; Wang, B. D.; Li, B.; Wang, Q.; Yang, Z. Y.; Li, T. R.; Li, Y. Crystal structures, DNA-binding and cytotoxic activities studies of Cu(II) complexes with 2-oxo-quinoline-3-carbaldehyde Schiff-bases. *Eur. J. Me. Chem.* 2010, 45, 5353-5361; and Tjioe, L.; Meininger, A.; Joshi, T.; Spiccia, L.; Graham, B. Efficient plasmid DNA cleavage by copper(II) complexes of 1,4,7-triazacyclononane ligands featuring xylyl-linked guanidinium groups. *Inorg. Chem.* 2011, 50, 4327-4339, each incorporated herein by reference in their entirety).

DNA binding experiments, which include absorption spectral titrations, fluorescence and circular dichroism, conformed to the standard methods and practices previously adopted by the laboratory (Marmur, J. A procedure for the isolation of deoxyribonucleic acid from microorganisms. *J. Mol. Biol.* 1961, 3, 208-218; Reicmann, E. M.; Rice, A. S.; Thomas, A. C.; Doty, P. A Further Examination of the Molecular Weight and Size of Desoxypentose Nucleic Acid. *J. Am. Chem. Soc.* 1954, 76, 3047-3053; and Chauhan, M.; Banerjee, K.; Arjmand, F. DNA binding Studies of Novel Copper(II) Complexes Containing L-tryptophan as Chiral Auxiliary. In vitro Antitumor Activity of Cu—Sn$_2$ Complex in Human Neuroblastoma Cells. *Inorg. Chem.* 2007, 46, 3072-3082, each incorporated herein by reference in their entirety).

Figures 9E, 9F:
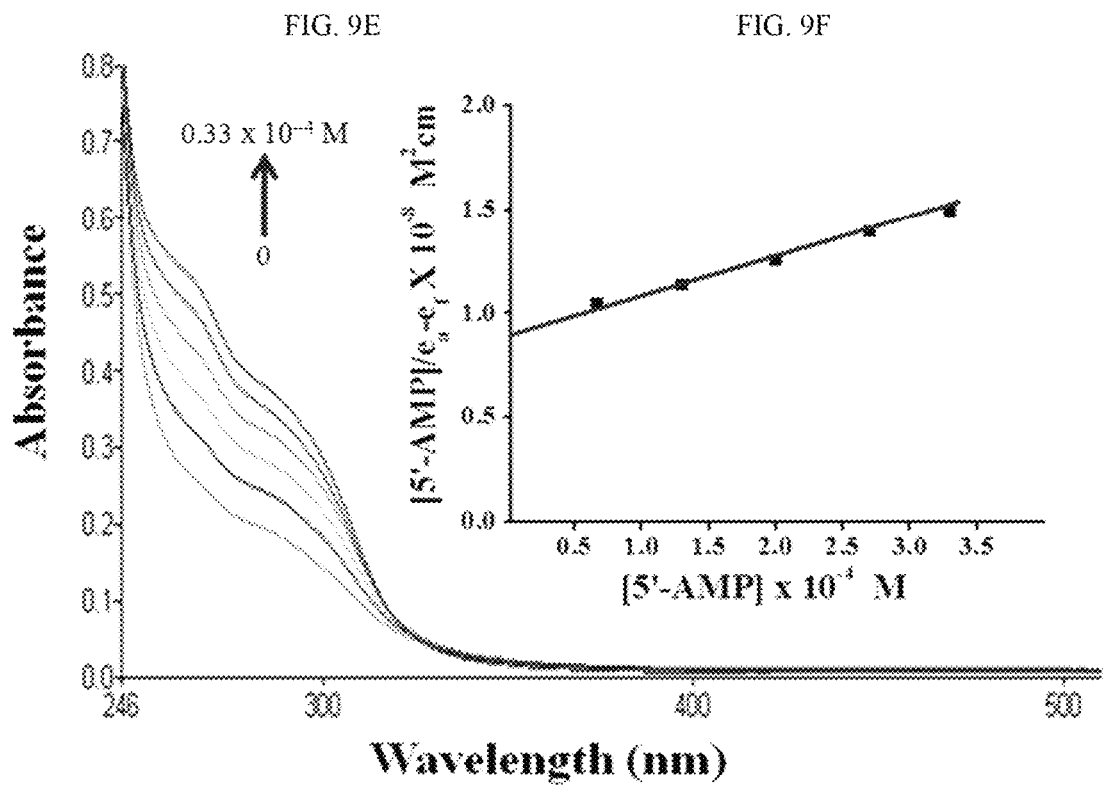
FIG. 9E is an overlay of the absorption spectra of complex 4 in Tris-HCl buffer at various concentrations of 5'-AMP at 25° C.
FIG. 9F is a plot of $[5'-AMP]/(e_a-e_f)$ against [5'-AMP] for the titration of 5'-AMP with complex 4.
Figures 9G, 9H:
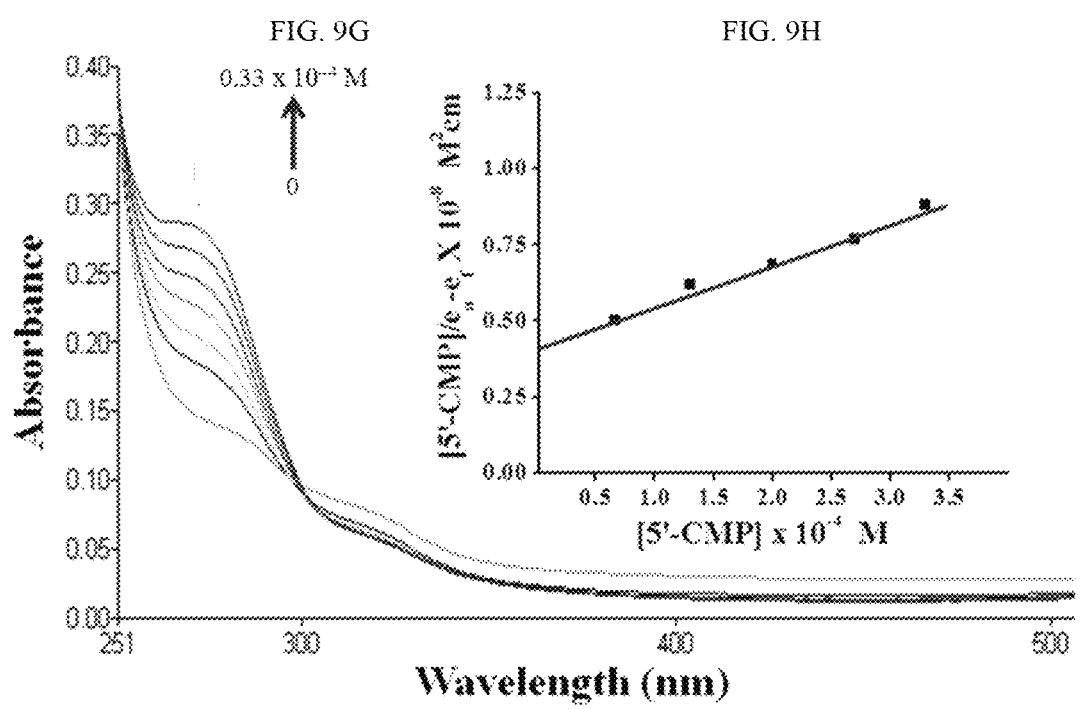
FIG. 9G is an overlay of the absorption spectra of complex 4 in Tris-HCl buffer at various concentrations of 5'-CMP at 25° C.
FIG. 9H is a plot of [5'-CMP]/($e_a-e_f$) against [5'-CMP] for the titration of 5'-CMP with complex 4.
Figure 10A:
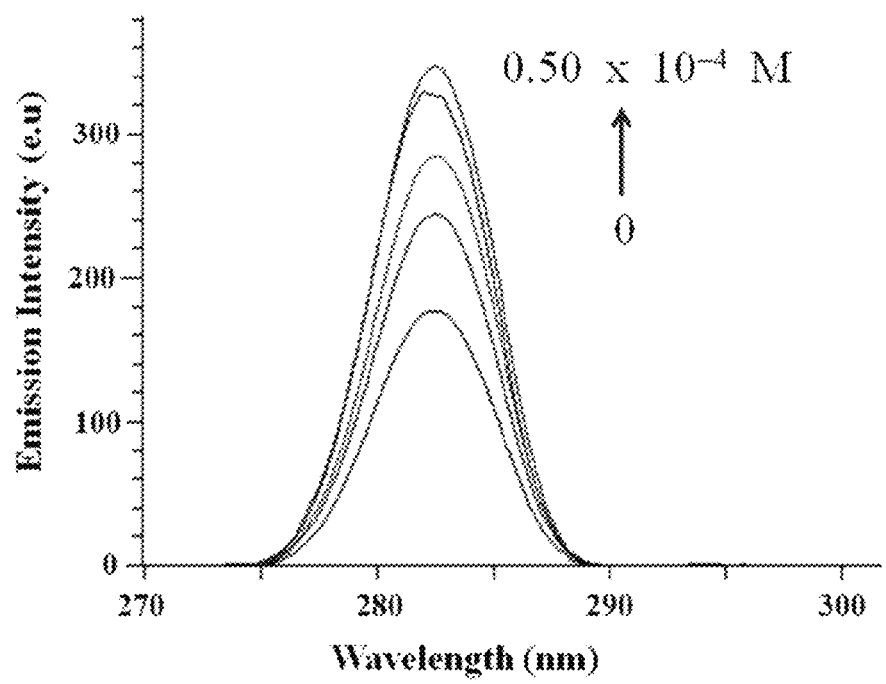
FIG. 10A is an overlay of the emission spectra of complex 1 in Tris-HCl buffer (pH=7.2) in the absence and presence of CT DNA.
Figure 10B:
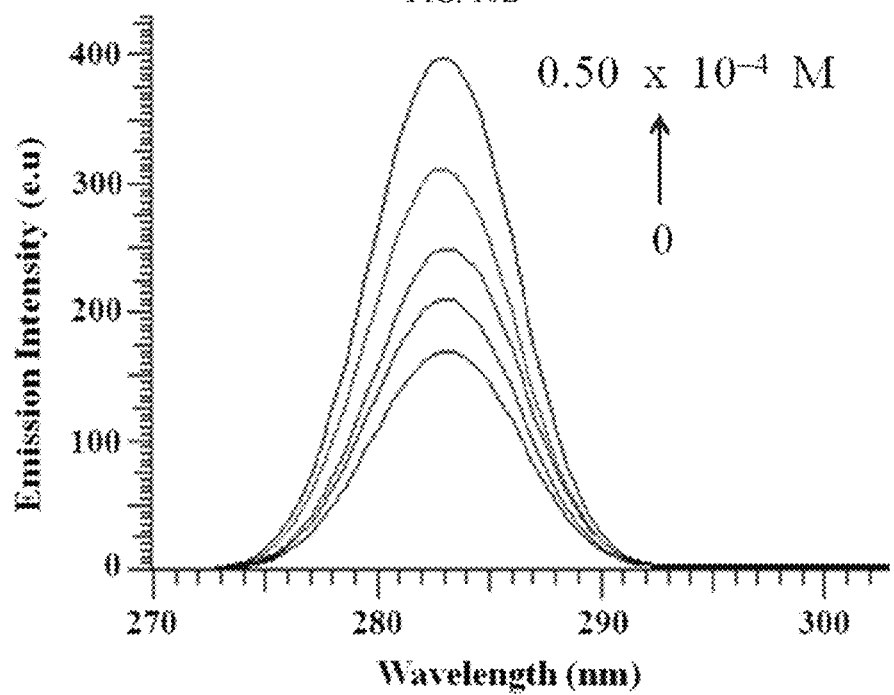
FIG. 10B is an overlay of the emission spectra of complex 2 in Tris-HCl buffer (pH=7.2) in the absence and presence of CT DNA.
Figure 10C:
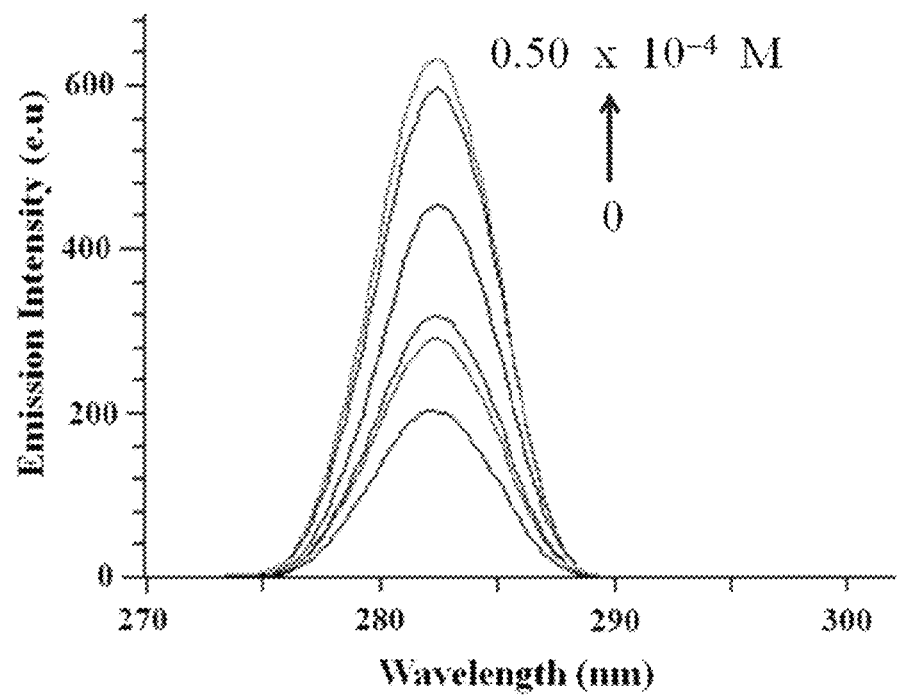
FIG. 10C is an overlay of the emission spectra of complex 3 in Tris-HCl buffer (pH=7.2) in the absence and presence of CT DNA.
Figure 10D:
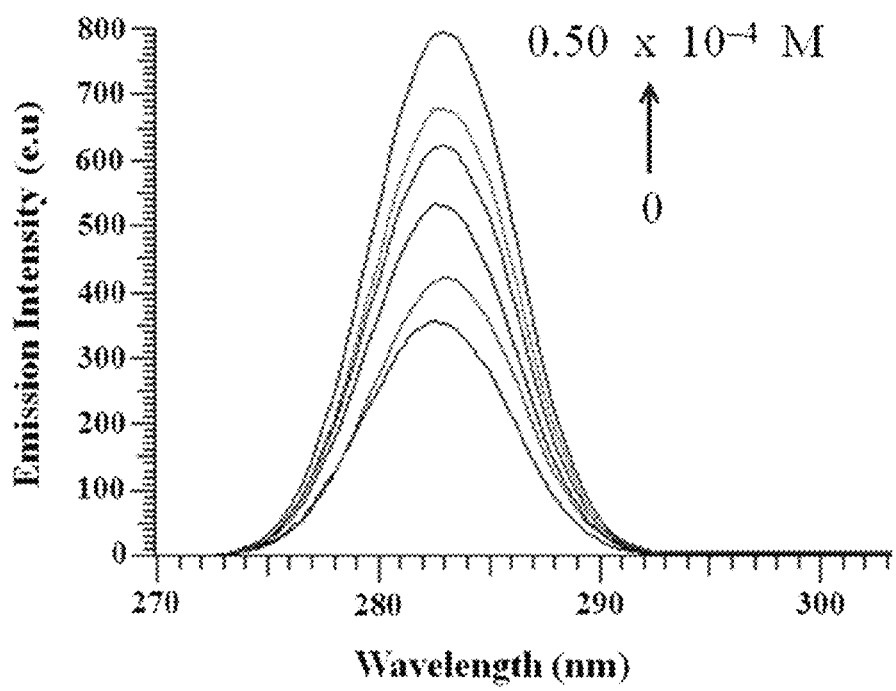
FIG. 10D is an overlay of the emission spectra of complex 4 in Tris-HCl buffer (pH=7.2) in the absence and presence of CT DNA.
Figure 10E:
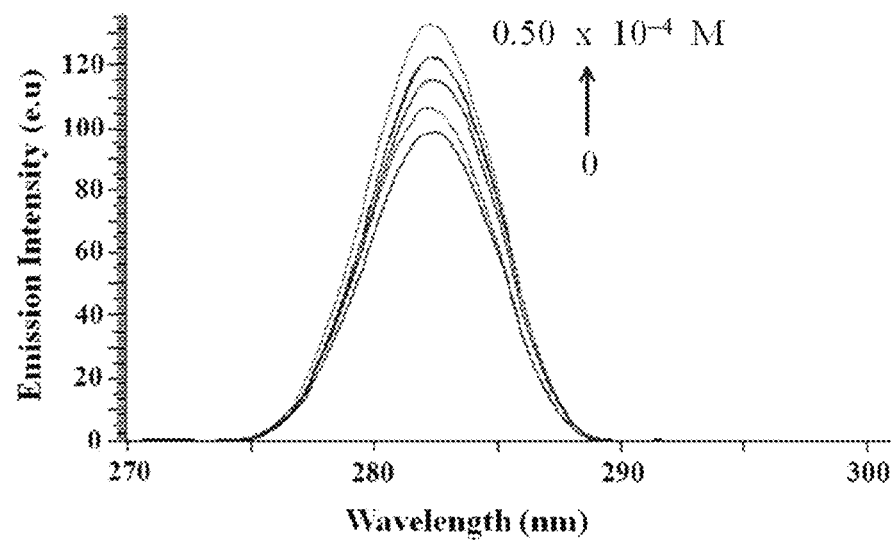
FIG. 10E is an overlay of the emission spectra of complex 5 in Tris-HCl buffer (pH=7.2) in the absence and presence of CT DNA.

To obtain concrete information and to determine the coordination of the metal ion to the specific site at the molecular target, interactions with low molecular building blocks of large DNA molecules viz., 5'-GMP, 5'-TMP, 5'-AMP and 5'-CMP were carried out with complex 4. On addition of increasing amounts (0.067×10$^{-4}$ M to 0.33×10$^{-4}$ M) of the mononucleosides to complex 4, hypochromic effect was observed with concomitant moderate blue shift (2-5 nm) at $\pi \rightarrow \pi^*$ (FIG. 9), indicating the electrostatic surface binding interactions of 4 with different nucleotides. The purine and pyrimidine bases of CT-DNA became exposed because of the unwinding of the DNA duplex promoting an effective binding to these base pairs with the drug entities. To compare quantitatively the binding of complex 4 to mononucleotides (5'-GMP, 5'-TMP, 5'-AMP and 5'-CMP), the intrinsic binding constants (K$_b$) were determined and found to be 3.3×10$^4$ M$^{-1}$, 4.9×10$^4$ M$^{-1}$, 5.7×10$^4$ M$^{-1}$, and 2.8×10$^4$ M$^{-1}$, respectively. The trend of mononucleotide interaction with 4, as validated by K$_b$ values was 5'-AMP>5'-TMP>5'-GMP>5'-CMP, supports the preferential selectivity for thymidine residue by the coordination with N3 atom of the thymine base of DNA duplex.

EXAMPLE 12

Absorption Spectral Experiments

Absorption spectral titration experiments were performed at a constant concentration of the complexes with varying CT-DNA concentrations. The absorbance (A) of the most shifted band of the investigated complexes was recorded after successive addition of CT-DNA. A reference cell containing DNA alone was used to nullify the absorbance due to the DNA at the measured wavelength. From the absorption titration data, the intrinsic binding constant (K$_b$) of the complexes with CT-DNA were determined using Wolfe-Shimmer equation (Wolfe, A.; Shimer, H. G.; Meehan, T. Polycyclic aromatic hydrocarbons physically intercalate into duplex regions of denatured DNA. *Biochem.* 1987, 26, 6392-6396, incorporated herein by reference in its entirety).

$$\frac{[DNA]}{\varepsilon_a - \varepsilon_f} = \frac{[DNA]}{\varepsilon_b - \varepsilon_f} + \frac{1}{K_b(\varepsilon_a - \varepsilon_f)} \quad (1)$$

$\varepsilon_a$, $\varepsilon_f$ and $\varepsilon_b$ correspond to $A_{obsd}$/[Complex], the extinction coefficient for free complex, and the extinction coefficient for the complexes in the fully bound form, respectively. A plot of [DNA]/$\varepsilon_a$-$\varepsilon_f$ vs. [DNA], where [DNA] is the concentration of DNA in the base pairs, gives $K_b$ as the ratio of slope to the intercept.

To evaluate the mode of interaction of the complexes with CT-DNA, absorption titration studies have been performed by monitoring the changes in absorption intensity by aliquot addition of DNA. On addition of increasing concentrations (0-1.2×10$^{-4}$ M) of CT DNA to a fixed amount (0.67×10$^{-4}$ M) of complexes 1-5, there was a change in absorption intensity in ligand-based π→π* transitions centered at ca. 270 nm, thus significant "hyperchromism" (43-20%) was observed along with blue shift of 5-2 nm (FIGS. 8A, 8C, 8E, 8G, and 8I). The resultant hyperchromic shift suggested that all the complexes were bound to CT-DNA by external contact, possibly due to electrostatic binding (Long, C. E.; Barton, K. On demonstrating DNA interaction. *J. Acc. Chem. Res.* 1990, 23, 271, incorporated herein by reference in its entirety). The intrinsic binding constant, $K_b$, is a useful tool to monitor the magnitude of the binding strength of complexes with CT-DNA (Table 12). The $K_b$ values followed the order 4>3>2>1>5, indicating that the complex 4 bound stronger to CT-DNA than other complexes. The relative difference in the $K_b$ values could be attributed to different binding modes of Au(I) complexes depending upon the type of substituent groups. Since lipophilicity and hydrophilicity of the gold complexes are important parameters which affect biodistribution, activity and selectivity of the drugs, the nature of the ligands attached to the gold atom is an important parameter in drug design. Previous structure-activity relationship studies on linear gold(I) complexes indicated that the presence of the phosphine ligand is important for the biological potency of the complexes (Mirabelli, C. K.; Johnson, R. K.; Hill, D. T.; Faucette, L. F.; Girard, G. R.; Kuo, G. Y.; Sung, C. M.; Crooke, S. T. Correlation of the in vitro cytotoxic and in vivo antitumor activities of gold(I) coordination complexes. *J. Med. Chem.* 1986, 29, 218-223, incorporated herein by reference in its entirety). Long alkyl chains lead to more hydrophobicity and consequently account for higher binding affinity with DNA compared to their short-chained analogs. This could be the reason for the higher binding affinity of complex 4. However, in complex 5, the bulky isopropyl moiety on the phosphine ligand could induce steric constraints resulting in the lower binding propensity with DNA.

EXAMPLE 13

Fluorescence Spectral Studies

Fluorescence experiments were carried out at a constant concentration of the complexes with increasing CT-DNA concentrations. The binding constant, K, of the gold(I) complexes was determined from Scatchard eqs. (2) and (3) by employing emission titration (Liu, D. G.; Liao, P. J.; Fang, Z. Y.; Huang, S. S.; Sheng, L. G.; Yu, Q. R. Interaction of bis(ethylene)tin(bis(salicylidene)ethylenediamine) with DNA. *Anal. Sci.* 2002, 18 391-395; and Healy, F. E. Quantitative determination of DNA-ligand binding using fluorescence spectroscopy. *J. Chem. Educ.* 2007, 84, 1304-1307, each incorporated herein by reference in their entirety).

$$C_F = C_T(I/I_o - P)(1-P) \quad (2)$$

$$r/C_F = K(n-r) \quad (3)$$

where $C_F$ is the free probe (i.e. free metal complex) concentration, $C_T$ is the total concentration of the probe added, I and $I_o$ are fluorescence intensities in the presence and absence of CT-DNA, respectively, r denotes a ratio of $C_B$ ($C_B = C_T - C_F$) to the DNA concentration, i.e., the bound probe concentration to the DNA concentration, K is the binding constant, "n" is the binding site number, and P is the ratio of the observed fluorescence quantum yield of the bound probe to that of the free probe. The value P was obtained as the intercept by extrapolating from a plot of I/$I_o$ vs. 1/[DNA].

Luminescence titrations involving quenching experiments were conducted by adding increasing concentration of the complexes to a fixed concentration of EB-DNA system. The Tris-HCl buffer was used as a blank to make preliminary adjustments. The Stern-Volmer quenching constant, $K_{SV}$ was obtained from the following equation (Lakowiez, R. J.; Webber, G. Quenching of fluorescence by oxygen. Probe for structural fluctuations in macromolecules. *Biochem.* 1973, 12, 4161-4170, incorporated herein by reference in its entirety).

$$I_o/I = 1 + K_{SV} \cdot r \quad (4)$$

where r is the ratio of total concentration of complex to that of DNA, and $I_o$ and I are the fluorescence intensities of EB in the absence and presence of complex.

The fluorescence emission titration of complexes 1-5 was carried out in order to understand the nature of binding mode of these complexes with CT-DNA. This method is highly sensitive, reproducible, and accurate. In the absence of CT-DNA, all complexes 1-5 (concentration=1.3×10$^{-4}$ M) emitted strong luminescence when excited at 275 nm in Tris-HCl/NaCl buffer with an emission maximum appearing at 340 nm. However, the subsequent addition of CT-DNA from 0.067-0.5×10$^{-4}$ M caused a gradual enhancement in the fluorescence intensity of the complexes with no apparent

TABLE 12

The intrinsic binding constant ($K_b$) values of complexes with CT DNA (mean standard deviation of ± 0.11)

| Complex | $K_b$ (M$^{-1}$) | λ(nm) | Hyperchromism (%) | Blue shift (nm) |
|---|---|---|---|---|
| (Me)$_3$PAu(S$_2$CN{Me}$_2$) (1) | 3.90 × 10$^4$ | 270 | 22 | 2 |
| (Et)$_3$PAu(S$_2$CN{Me}$_2$) (2) | 4.74 × 10$^4$ | 270 | 31 | 3 |
| (Me)$_3$PAu(S$_2$CN{Et}$_2$) (3) | 6.81 × 10$^4$ | 272 | 37 | 3 |
| (Et)$_3$PAu(S$_2$CN{Et}$_2$) (4) | 8.53 × 10$^4$ | 272 | 43 | 5 |
| (i-Pr)$_3$PAu(S$_2$CN{Me}$_2$) (5) | 2.48 × 10$^4$ | 270 | 20 | 0 | change in the shape and position of the emission bands (FIGS. 10A-10E), which is indicative of a strong interaction of the Au(I) drug entities with CT DNA. The hydrophobic molecular structure of CT DNA could be responsible for enhancing the fluorescence quantum yield of complexes, leading to the higher fluorescence intensity with increasing concentration of CT DNA. In addition, energy transfer from CT-DNA to metal complexes could also induce fluorescence enhancement (Arjmand, F.; Jamsheera, A.; Afzal, M.; S. Tabassum, S. Enantiomeric Specificity of Biologically Significant Cu(II) and Zn(II) Chromone Complexes Towards DNA. *Chirality.* 2012, 24, 977-986, Tabassum, S.; Yadav, S.; Arjmand, F. Synthesis and mechanistic insight of glycosylated $Cu^{II}/Ni^{II}$—$Sn_2^{IV}$ heterobimetallic DNA binding agents: Validation of a specific $Cu^{II}$—$Sn_2^{IV}$ chemotherapeutic agent for human leukemic cell line K-562. *J. Organomet. Chem.* 2013, 745-746, 226-234, incorporated herein by reference in its entirety). The Scatchard binding constants, K, of 1-5 were found to be $2.8\times10^4$ $M^{-1}$, $3.5\times10$ $M^{-1}$, $5.7\times10$ $M^{-1}$, $6.6\times10$ $M^{-1}$, and $1.9\times10^4$ $M^{-1}$, respectively with mean standard deviations of ±0.07. These results were consistent with the findings obtained from UV-vis spectral studies.

A reliable method for studying the binding of molecules to nucleic acids is the fluorescence quenching method. Ethidium bromide (EB) is a planar cationic dye which is widely used as a sensitive fluorescence probe for native DNA. EB emits intense fluorescent light in the presence of DNA due to its strong intercalation between the adjacent DNA base pairs. The displacement technique is based on the decrease of fluorescence resulting from the displacement of EB from a DNA sequence by a quencher, and the quenching is due to the reduction of the number of binding sites on the DNA that are available to the EB (Ramachandran. E.; Raja, S. D.; Bhuvanesh, P. S. N.; Natarajan, K. Mixed ligand palladium(II) complexes of 6-methoxy-2-oxo-1,2-dihydroquinoline-3-carbaldehyde 4N-substituted thiosemicarbazones with triphenylphosphine co-ligand: Synthesis, crystal structure and biological properties. *Dalton Trans.* 2012, 41 13308-13323, incorporated herein by reference in its entirety). Upon increasing concentrations of complexes 1-5, the fluorescence intensity of CT DNA previously treated with EB at 585-590 nm showed a remarkable decreasing trend, suggesting that the Au(I) analogs bind significantly to DNA. Furthermore, the quenching extents were quantitatively evaluated by employing Stern-Volmer equation and $K_{SV}$ values for 1-5 were found to be 0.19, 0.34, 0.67, 0.91 and 0.10, respectively. From the above data, it is clear that 4 replaces EB more effectively than other complexes, and this observation agreed with the results obtained from electronic absorption studies.

In summary, the synthesized complexes 1-5 exhibit structural novelty: (i) a biologically active pharmacophore that could facilitate the transport of gold to the target site, and (ii) the presence of a linear S—Au—$PR_3$ moiety that could act selectively in cancer tissues and could undergo biological ligand exchange reactions, thereby exhibiting potent cytotoxic activity. For example, the $PR_3$ ligand may be exchanged/replaced by DNA. The complexes showed significant cytotoxic effects and were found to be more active than cisplatin.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. A DNA/dithiocarbamato(phosphine)metal complex, comprising:
   a dithiocarbamato(phosphine)gold(I) compound represented by formula (I):

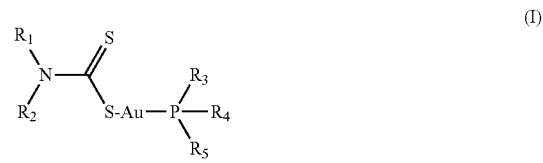

(I)

a salt thereof, a solvate thereof, or a combination thereof; and
   DNA complexed to the dithiocarbamato(phosphine)gold (I) compound;
   wherein $R_1$ and $R_2$ are alkyl groups independently selected from the group consisting of methyl, ethyl, and isopropyl;
   $R_3$, $R_4$, and $R_5$ are independently selected from the group consisting of an optionally substituted $C_1$-$C_3$ alkyl, an optionally substituted arylalkyl, an optionally substituted aryl, an optionally substituted vinyl, an optionally substituted alkoxy, and an optionally substituted aryloxy; and
   with the proviso that $R_1$, $R_2$, $R_3$, $R_4$, and $R_5$ are not each an ethyl.

2. The DNA/dithiocarbamato(phosphine)metal complex of claim 1, wherein $R_1$ and $R_2$ are the same unsubstituted alkyl group, and $R_3$, $R_4$, and $R_5$ are the same optionally substituted $C_1$-$C_3$ alkyl group.

3. The DNA/dithiocarbamato(phosphine)metal complex of claim 2, wherein $R_1$ and $R_2$ are ethyls, and $R_3$, $R_4$, and $R_5$ are methyls.

4. The DNA/dithiocarbamato(phosphine)metal complex of claim 1, wherein $R_3$, $R_4$, and $R_5$ are a $C_1$-$C_2$ alkyl group.

5. The DNA/dithiocarbamato(phosphine)metal complex of claim 1, wherein $R_1$ and $R_2$ are methyls and $R_3$, $R_4$, and $R_5$ are ethyls.

* * * * *